(12) United States Patent
Smaldone et al.

(10) Patent No.: US 10,004,858 B2
(45) Date of Patent: *Jun. 26, 2018

(54) METHODS, DEVICES AND FORMULATIONS FOR TARGETED ENDOBRONCHIAL THERAPY

(71) Applicant: The Research Foundation of State University of New York, Albany, NY (US)

(72) Inventors: Gerald C. Smaldone, Setauket, NY (US); Lucy B. Palmer, Nissequoque, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 197 days.

This patent is subject to a terminal disclaimer.

(21) Appl. No.: 13/932,757

(22) Filed: Jul. 1, 2013

(65) Prior Publication Data

US 2013/0298904 A1 Nov. 14, 2013

Related U.S. Application Data

(60) Continuation of application No. 11/062,519, filed on Feb. 22, 2005, now Pat. No. 8,602,023, which is a
(Continued)

(51) Int. Cl.
*A61M 15/00* (2006.01)
*A61M 11/06* (2006.01)
(Continued)

(52) U.S. Cl.
CPC .......... *A61M 15/009* (2013.01); *A61M 11/00* (2013.01); *A61M 11/06* (2013.01);
(Continued)

(58) Field of Classification Search
CPC .. A61M 11/00; A61M 11/001; A61M 11/005; A61M 11/007; A61M 11/02;
(Continued)

(56) References Cited

U.S. PATENT DOCUMENTS 3,788,326 A * 1/1974 Jacobs ................. A61M 16/00
128/207.15
3,794,026 A * 2/1974 Jacobs ................. A61M 16/00
128/200.13
(Continued)

FOREIGN PATENT DOCUMENTS

WO WO/2004/071368 8/2004

OTHER PUBLICATIONS

"Amoxicillin Trihydrate" PubChem. National Center for Biotechnology Information. https://pubchem.ncbi.nlm.nih.gov/compound/Amoxicillin_trihydrate#section=Top Accessed Jul. 25, 2017.*
(Continued)

*Primary Examiner* — Annette Dixon
(74) *Attorney, Agent, or Firm* — Medlen & Carroll, LLP

(57) ABSTRACT

The present invention provides an improved means of treating tracheobronchitis, bronchiectasis and pneumonia in the nosocomial patient, preferably with aerosolized anti gram-positive and anti-gram negative antibiotics administered in combination or in seriatim in reliably sufficient amounts for therapeutic effect. In one aspect, the invention assures this result when aerosol is delivered into the ventilator circuit. In one embodiment the result is achieved mechanically. In another embodiment, the result is achieved by aerosol formulation. In another aspect, the invention assures the result when aerosol is delivered directly to the airways distal of the ventilator circuit. The treatment means eliminates the dosage variability that ventilator systems engender when aerosols are introduced via the ventilator
(Continued)

circuit. The treatment means also concentrates the therapeutic agent specifically at affected sites in the lung such that therapeutic levels of administered drug are achieved without significant systemic exposure of the patient to the drug. The invention further provides a dose control device to govern this specialized regimen.

14 Claims, 21 Drawing Sheets

Related U.S. Application Data division of application No. 10/430,658, filed on May 6, 2003, now Pat. No. 7,334,580.

(60) Provisional application No. 60/378,475, filed on May 7, 2002, provisional application No. 60/380,783, filed on May 15, 2002, provisional application No. 60/420,429, filed on Oct. 22, 2002, provisional application No. 60/439,894, filed on Jan. 14, 2003, provisional application No. 60/442,785, filed on Jan. 27, 2003.

(51) Int. Cl.
*A61M 16/04* (2006.01)
*A61M 16/08* (2006.01)
*A61M 11/00* (2006.01)
*A61M 16/00* (2006.01)

(52) U.S. Cl.
CPC ........ *A61M 16/0057* (2013.01); *A61M 16/04* (2013.01); *A61M 16/0463* (2013.01); *A61M 16/0484* (2014.02); *A61M 16/08* (2013.01); *A61M 16/0808* (2013.01); *A61M 16/0833* (2014.02); *A61M 16/0465* (2013.01)

(58) Field of Classification Search
CPC .. A61M 11/04; A61M 11/041; A61M 11/042; A61M 11/06; A61M 15/00; A61M 15/0025; A61M 15/0026; A61M 15/0065; A61M 15/0085; A61M 15/0086; A61M 15/009; A61M 16/0057; A61M 16/04; A61M 16/0463; A61M 16/0465; A61M 16/0484; A61M 16/08; A61M 16/0808; A61M 16/0816; A61M 16/0833; A61M 16/10; A61M 16/1065; A61M 16/16; A61M 16/162; A61M 16/20; A61M 16/208; A61M 2016/0021; A61M 2016/0027; A61M 2202/064; A61M 2205/073; A61M 2205/3561; A61M 2205/3569; A61M 2205/8206; A61M 2206/16; A61M 2209/08; A61M 2209/082
USPC ............ 128/200.11, 200.13, 200.14, 200.16, 128/200.18, 200.21, 200.23, 200.24, 128/202.27, 203.12, 203.15, 203.16, 128/203.18, 203.22, 203.28, 204.18, 128/204.21, 204.22, 205.24, 207.17, 128/207.18, 912; 239/1, 102.1, 102.2, 239/142, 338, 5, 505, 507, 8, 99
See application file for complete search history.

(56) References Cited

U.S. PATENT DOCUMENTS

| | | | | |
|---|---|---|---|---|
| 4,310,509 | A | 1/1982 | Berglund et al. | 424/28 |
| 4,643,181 | A | 2/1987 | Brown | 128/156 |
| 5,049,389 | A * | 9/1991 | Radhakrishnan | A61K 9/0078 264/4.1 |
| 5,508,269 | A * | 4/1996 | Smith | A61K 9/0078 514/38 |
| 5,512,055 | A | 4/1996 | Shikani et al. | 604/265 |
| 5,531,219 | A * | 7/1996 | Rosenberg | A61K 9/007 128/203.12 |
| 5,642,730 | A | 7/1997 | Baran | 128/207.14 |
| 5,666,946 | A * | 9/1997 | Langenback | A61M 15/0085 128/200.14 |
| 5,762,638 | A | 6/1998 | Shikani et al. | 604/265 |
| 5,964,223 | A | 10/1999 | Baran | 128/207.14 |
| 6,014,972 | A * | 1/2000 | Sladek | A61M 15/0065 128/203.12 |
| 6,041,777 | A * | 3/2000 | Faithfull | A61M 16/0054 128/200.24 |
| 6,079,413 | A | 6/2000 | Baran | 128/207.14 |
| 6,210,359 | B1 | 4/2001 | Patel et al. | 604/68 |
| 6,235,177 | B1 * | 5/2001 | Borland | B05B 17/0638 205/122 |
| 6,293,279 | B1 | 9/2001 | Schmidt et al. | 128/200.23 |
| 6,293,474 | B1 * | 9/2001 | Helf | A01M 1/205 239/102.1 |
| 6,296,196 | B1 * | 10/2001 | Denen | A01M 1/205 239/102.1 |
| 6,378,780 | B1 * | 4/2002 | Martens, III | B05B 17/0684 239/102.2 |
| 6,403,057 | B1 | 6/2002 | Schneider et al. | 424/9.52 |
| 6,615,824 | B2 * | 9/2003 | Power | A61M 15/0085 128/200.14 |
| 6,978,779 | B2 * | 12/2005 | Haveri | A61M 15/0085 128/200.14 |
| 8,602,023 | B2 * | 12/2013 | Smaldone | A61M 11/06 128/200.14 |
| 2001/0042794 | A1 * | 11/2001 | Tomkins | A01M 1/205 239/102.2 |
| 2002/0002975 | A1 * | 1/2002 | Power | A61M 15/0085 128/203.12 |
| 2003/0073625 | A1 * | 4/2003 | Redman | A61K 38/10 514/2.3 |
| 2004/0011358 | A1 | 1/2004 | Smaldone et al. | 128/207.14 |
| 2005/0235987 | A1 | 10/2005 | Smaldone et al. | 128/202.27 |
| 2014/0014103 | A1 * | 1/2014 | Smaldone | A61M 16/14 128/203.12 |

OTHER PUBLICATIONS

Combes, A. et al. (2002) "Incidence and outcome of polymicrobial ventilator-associated pneumonia," *Chest* 121(5), 1618-1623.
Dolovich, M. A. et al. (2000) "Consensus statement: aerosols and delivery devices. American Association for Respiratory Care," *Respir. Care* 45(6), 589-596.
Fuller, H. D. et al. (1990) "Pressurized Aerosol versus Jet Aerosol Delivery to Mechanically Ventilated Patients Comparison of Dose to the Lungs," *Am. Rev. Respir. Dis.* 141(2), 440-444.
Hoffken, G. et al. (2002) "Nosocomial pneumonia: the importance of a de-escalating strategy for antibiotic treatment of pneumonia in the ICU," *Chest* 122(6), 2183-2196.
Levy, J. et al. (1983) "Bioactivity of Gentamicin in Purulent Sputum from Patients with Cystic Fibrosis or Bronchiectasis: Comparison with Activity in Serum," *J. Infect. Dis.* 148(6), 1069-1076.
Palmer, L. B. et al. (1998) "Aerosolized antibiotics in mechanically ventilated patients: delivery and response," *Crit. Care Med.* 26(1), 31-39.
Pennington, J. E. (1981) "Penetration of Antibiotics into Respiratory Secretions," *Rev. Infect. Dis.* 3(1), 67-73.
U.S. Appl. No. 60/378,485, filed May 6, 2002, Chen, S.
U.S. Appl. No. 60/380,783, filed May 15, 2002, Smaldone, G.C. et al.
U.S. Appl. No. 60/420,429, filed Oct. 22, 2002, Smaldone, G.C. et al.
U.S. Appl. No. 60/439,894, filed Jan. 14, 2003, Smaldone, G.C. et al.
U.S. Appl. No. 60/442,785, filed Jan. 27, 2003, Smaldone, G.C. et al.
Ramsey, B. W. et al. (1999) "Intermittent Administration of Inhaled Tobramycin in Patients with Cystic Fibrosis," *N. Engl. J. Med.* 340(1), 23-30.

(56) References Cited

OTHER PUBLICATIONS

Rello, J. et al. (2002) "Epidemiology and outcomes of ventilator-associated pneumonia in a large US database," *Chest* 122(6), 2115-2121.

* cited by examiner

BENCH MODEL FOR AEROSOL DELIVERY DURING MECHANICAL VENTILATION (SCHEMATIC)

FIG. 16A

BENCH MODEL FOR AEROSOL DELIVERY DURING MECHANICAL VENTILATION (SCHEMATIC)

Expiratory line
Inspiratory line
Expiratory line filter
Y piece
ET tube
Trudell catheter location
Model of proximal airways
Inhaled mass filter
to lung

FIG. 16B

METHODS, DEVICES AND FORMULATIONS FOR TARGETED ENDOBRONCHIAL THERAPY

This application is a continuation of, and claims priority to, U.S. patent application Ser. No. 11/062,519, filed Feb. 22, 2005, now issued U.S. Pat. No. 8,602,023, which is a divisional of, and claims priority to, U.S. patent application Ser. No. 10/430,658, filed May 6, 2003, now U.S. Pat. No. 7,334,580. Both applications are incorporated herein, entirety by reference, and both applications claim priority to U.S. Provisional Application Ser. No. 60/378,485 filed on 05/07/02 and 60/380,783 filed 05/15/02 and 60/420,429 filed on 10/22/02 and 60/439,894 filed on 01/14/03 and 60/442,785 filed on 01/27/03, under 35 U.S.C. 11(b), the contents of which are incorporated herein in their entirety.

FIELD OF THE INVENTION

The invention relates to methods and compositions for treating tracheobronchitis, bronchiectasis and pneumonia in subjects, including the hospital patient. The present invention also relates to prevention of pulmonary infections in patients at increased risk for such infections, particularly intubated patients, through the delivery of antimicrobials to the trachea (and in some embodiments to the deep lung). In particular, the invention provides a means for treating a mechanically ventilated patient with an aerosolized antimicrobial agent without exposing such patient to significant systemic levels of the agent. Especially, the invention provides a means for administering to mechanically ventilated patients a dose of the therapeutic agent that is substantially invariant from patient-to-patient when compared to the variances typical for aerosolized agents administered via the ventilator circuit. In another aspect, the invention relates to devices that ensure the dose-control of which the invention is capable. In a preferred embodiment, the present invention contemplates the use, in combination, of aerosolized antimicrobial agents capable in combination of exerting a bactericidal or bacteriostatic effect on gram-positive and gram-negative bacteria in the lung and tracheobronchial tree to treat or prevent pulmonary infections.

BACKGROUND OF THE INVENTION

Mechanical ventilation appears to upset the normal processes that keep the lungs free of disease. Indeed, ventilator-associated pneumonia (VAP) is reported to be the most common hospital-acquired infection among patients requiring mechanical ventilation. There is a strong correlation between the duration of intubation and development of infection. In a recent large study, the mean interval between intubation and the identification of VAP was 3.3 days. Rello J. et al., "Epidemiology and Outcomes of Ventilator-Associated Pneumonia in a Large US Database" Chest 122:2115 (2002). Importantly, once VAP develops, the patient usually requires a more extended period of ventilation. Unfortunately, prolonging the intubation invites new rounds of deep infection with further decompensation of respiratory function, in a vicious cycle ending frequently in death.

It is well-known to treat such infections with systemically administered antibiotics, but simultaneous treatment of the whole body with multiple antibiotic agents is fraught with complications that range from accelerating the selection of antibiotic-resistant strains to disrupting fluid and electrolyte balance and compromising the antiviral defense mechanisms of mucosal epithelia throughout the body. Systemically administered antibiotics can also have adverse effects on the liver, kidney and skeleton. Such concerns have resulted in a recent call for a de-escalating strategy for antibiotic administration. Hoffken G. and Niederman M. S., "Nosocomial Pneumonia: The Importance of De-escalating Strategy for Antibiotic Treatment of Pneumonia in the ICU" Chest 122:2183 (2002).

Exacerbating the risks cited above is the fact that the objective of systemic therapy is to achieve high concentrations of antibiotic not in the circulation but on the mucosal side of the bronchi, i.e., in the bronchial secretions. Many antibiotics diffuse poorly from the bloodstream across the bronchi [Pennington, J. E., "Penetration of antibiotics into respiratory secretions," Rev Infect Dis 3(1):67-73 (1981)], which leads the practitioner to administer higher doses of antibiotic than would be prescribed for a truly systemic infection. Moreover, the purulent sputum that characterizes infected patients tends to compromise the potency of many antibiotics. See e.g., Levy, J., et al., "Bioactivity of gentamicin in purulent sputum from patients with cystic fibrosis or bronchiectasis: comparison with activity in serum," J Infect Dis 148(6):1069-76 (1983). This factor further motivates the practitioner to prescribe large amounts of antibiotic. These dangers have led some experts to propose that treating lung infections systemically in nosocomial patients should be abandoned. Unfortunately, known alternatives are not attractive either.

An alternative approach in which antibiotics are applied to the oral, gastric and endobronchial mucosa along with systemic administration has been tried. It is very costly and, in any case, is not associated with any ameliorating effect on mortality. It also invites "outbreaks" of antibiotic-resistant infections in intensive care units especially when used indiscriminately.

In another effort to overcome the aforementioned problems associated with systemic administration, various attempts have been made to administer antibiotics directly to the mucosal surface of the lungs of spontaneously breathing patients in aerosols (liquid droplets or dry powders) delivered via various nebulizers. However, more localized administration of antibiotics is controversial. Early studies with aerosolized antimicrobials did not show unambiguously positive results. This may be due, however, to a poor appreciation of the physics of aerosol administration to the intubated patient. It is now recognized that poor system designs and/or improper device usage can result in virtually no aerosol reaching the desired sites in the lungs. "Consensus Statement: Aerosols and Delivery Devices" Respiratory Care 45:589 (2000).

Moreover, even in studies with generally satisfactory results in terms of levels of antibiotic achieved or the reduction in bacterial load observed [Eisenberg, J., et al., "A comparison of peak sputum tobramycin concentration in patients with cystic fibrosis using jet and ultrasonic nebulizer systems. Aerosolized tobramycin study group," Chest 111(4):955-962 (1997); Ramsey, B. W., et al., "Intermittent administration of inhaled tobramycin in patients with cystic fibrosis. Cystic fibrosis inhaled tobramycin study group," N Engl J Med 340(1):23-30 (1999)], no effort was made to reduce the amount of antibiotic administered—the nebulizers were charged with quantities of antibiotic equivalent to doses typically administered systemically.

The administration of antibiotics by nebulization, in ventilated patients is reportedly even less satisfactory (Fuller, H. D., et al., Pressurized aerosol versus jet aerosol delivery to mechanically ventilated patients. Am. Rev. Respir Dis 1989, 141:440-444; MacIntyre, N., et al., Aerosol delivery to intubated, mechanically ventilated patients. *Crit. Care Med* 1985, 13:81-84). In ventilated patients, nebulization that bypasses the humidifier and is actuated only on the inspiration phase of the breathing cycle has been attempted using a ventilator (Bear II, Bear Medical Systems, Riverside, Calif.) of obsolete design (Palmer, et al., *Crit. Care Med* 1998, 26:31-39).

The extreme variability in effective dose that known methods of aerosol delivery engender is not important for conventional drugs such as bronchodilators because of the potency and safety of such agents. Variability is a crucial problem, however, in the case of antibiotics. The risk of pulmonary toxicity discourages the prescription of heroic doses to overwhelm the variability problem. That leaves the patient exposed to the prospect of inadequate treatment, a particularly risky matter. In the worst cases, by the time the insufficiency is recognized, the opportunity to correct the situation is past. In many other cases, the insufficient treatment encourages the selection and growth of antibiotic-resistant organisms in the patient, which totally disarms the practitioner and exposes entire cohorts of patients to danger.

What is needed in the art to encourage the abandonment of systemic antibiotic therapy to treat lung infections in the nosocomial patient is a means of delivering antibiotics directly into the distal airways of the lung. Such means should produce reliably high titers of antibiotics in the bronchial secretions in a short period of time so as to overwhelm all infectious organisms before selection processes can even begin to establish a population of resistant organisms. On the other hand, the invention should provide a reliable means of dose control to avoid "spillover" into the systemic circulation, pulmonary toxicity, and inadvertent exposure of medical personnel and other patients to escaped antibiotics.

SUMMARY OF THE INVENTION

These and other objects are furnished by the present invention which provides a method for treating or preventing pulmonary infections, including nosocomial infections, in animals, including, especially, humans. The method generally comprises administering to an animal subject or human patient in need thereof, as an aerosol, a therapeutically effective amount of an antibiotic substance or a pharmaceutically acceptable salt thereof. Several antibiotics may be delivered in combination according to the invention, or in seriatim. Preferably, the amounts delivered to the airways, if delivered systemically in such amounts, would not be sufficient to be therapeutically effective and would certainly not be enough to induce toxicity. At the same time, such amounts will result in sputum levels of antibiotic of more than about 10-100 times the minimum inhibitory concentration ("MIC").

In one aspect, the therapeutically effective amount reaches the airways by means of a nebulizer positioned to direct its aerosol into the ventilator circuit. A variety of nebulizers suitable for creating aerosols as liquid droplets or dry particles are useful in the invention. In fact, any means of aerosol delivery that tends to minimize trapping of aerosol particles on the inner walls of the ventilator circuit is within the scope of the invention. In one embodiment, this object is achieved by insuring that the aerosolized particles are prevented from undergoing significant hygroscopic enlargement, since particles enrobed in water will tend to condense on the walls. In one embodiment, the step is introduced of reducing humidity in the ventilator circuit by a predetermined amount before nebulization begins. In this embodiment, according to the invention, a humidity that maintains mass median aerodynamic diameter ("MMAD") at less than about 3 µm as predetermined in a standard bench-test model is preferred, and an MMAD less than about 1.5 µm is more preferred. In another embodiment, each aerosol particle is delivered enrobed in a substantially anhygroscopic envelope.

Of course, embodiments can be used where diameters are greater. Moreover, in some cases, the present invention contemplates adjustments to the surface electrical charges on the particles or the walls. For example, assuming surface charge on the device is important, the present invention contemplates embodiments wherein the connectors are made, or the Y piece (discussed below) is made, of metal (or at least coated with metal). Alternatively, the plastic connectors and/or Y piece can be treated with agents (e.g. wetting agents, detergents, soaps) to adjust surface charge.

In another aspect of the invention, aerosolized antibiotic is delivered directly to the airways of the animal subject or human patient, largely by-passing the ventilator circuit. A particularly convenient means for delivering aerosolized antibiotic according to the invention is described in U.S. Pat. Nos. 5,642,730, 5,964,223 and 6,079,413, hereby incorporated by reference. Since the treatment strategy in which the instant invention is useful benefits from placement of a specialized suction catheter in the patient's airway as described below, one embodiment of this aspect of the instant invention is a combination aerosol and suction catheter.

Any such delivery device is within the scope of the invention if it is capable of delivering a predictable amount of a therapeutic agent within the ranges contemplated in the invention. Preferably, this requirement is achieved with a device for containing the prescribed amount of therapeutic agent, which device is another aspect of the invention. Such device, according to the invention, is sized to accommodate that specific quantity of antibiotic which, in a predetermined delivery period, will result in the delivery of a predetermined amount of antibiotic. Such device is designed to operatively fit an aerosol delivery device that is within the scope of the invention.

In one embodiment, the present invention contemplates a device comprising a fluid driving element attached to a dose metering element, said dose metering element engaged to an aerosolizing catheter. In a preferred embodiment, the dose metering element is detachably engaged to said aerosolizing catheter and comprises a reservoir of defined volume, said reservoir being preferably configured as a transparent or semi-transparent cylinder or tube, with or without visible measurement indicia. In this preferred embodiment, the fluid formulation (e.g. antibiotic formulation) for the patient is placed in the reservoir, the fluid driving element being disposed in relation to the reservoir such that, in operation, the fluid driving element urges the fluid formulation out of the reservoir and into the aerosolization device. In a preferred embodiment, the fluid driving element comprises a plunger or piston driven by compressed gas, said compressed gas stored in a container or canister and released by the operator of the device. When the release of compressed gas is triggered, the plunger or piston pushes the defined volume of the formulation into the aerosolizing catheter. In a particularly preferred embodiment, the device is a "stand alone" device configured such that it can engage an opening or port in a ventilation system, wherein said aerosolizing catheter is dimensioned to fit inside (or along side) an endotracheal tube (and/or tracheostomy tube) of an intubated patient, such that the delivery end (i.e. out of which the aerosol is delivered) of the catheter extends approximately to the end of the tube (or preferably below the end of the tube, thereby delivering aerosol in a manner that bypasses the tube). In a particularly preferred embodiment, the end of the aerosolizing catheter comprises a baffle to slow the speed of the aerosol.

In a preferred embodiment, the drug or drugs in the formulation are antimicrobials (i.e. antifungals, antivirals, and/or antibacterials). In a particularly preferred embodiment, the present invention contemplates a formulation comprising an anti-gram positive antibiotic substance together with an anti-gram-negative antibiotic substance, or pharmaceutically acceptable salts thereof, in an aerosolizing device. In one embodiment, the method comprises: a) providing: i) a patient (whether human or animal) exhibiting one or more symptoms of infection (or simply a patient at risk for infections); ii) a formulation (typically a liquid, dry powder or lipid formulation) comprising a first antibiotic having activity against gram positive bacteria and a second antibiotic having activity against gram negative bacteria; iii) an aerosol delivery device comprising an upper end and a lower end, said lower end comprising an aerosol delivery end configured to fit within said patient's trachea (or within the endotracheal or tracheostomy tube); b) inserting said aerosol delivery end of said device within said patient's trachea to create a positioned device; and c) aerosolizing said formulation under conditions such that said formulation is delivered through said aerosol delivery end of said positioned device to said patient, wherein said aerosol first contacts said patient at said patient's trachea (thereby bypassing the oro-pharynx). It is not intended that the above-mentioned embodiment of the present invention be limited by the delivery device. In one embodiment, said aerosol delivery device comprises an aerosol delivery catheter. In another embodiment, said aerosol delivery device comprises a bronchoscope fitted with an aerosolizing nozzle. In yet another embodiment, said aerosol delivery device comprises a metered dose inhaler fitted with a nozzle extension.

The embodiment of the method of administering a mixture of antibiotics is particularly appropriate for intubated patients. To that end, the present invention contemplates an embodiment of the method, comprising: a) providing: i) a patient (whether human or animal) exhibiting one or more symptoms of microbial infection (or simply a patient who— because of the intubation, or length of time intubated—is at risk for infection), said patient being intubated with a tube selected from endotracheal tubes and tracheostomy tubes, said tube having a lower end and an upper end; ii) a formulation (typically a liquid, dry powder or lipid formulation) comprising a first antibiotic having activity against gram positive bacteria and a second antibiotic having activity against gram negative bacteria; iii) an aerosol delivery catheter comprising an upper end and a lower end, said lower end comprising an aerosol delivery end configured to fit within said tube; b) inserting said aerosol delivery end of said catheter within said tube to create a positioned catheter; and c) aerosolizing said formulation under conditions such that said formulation is delivered through said positioned catheter to said patient. In a preferred embodiment, said tube is connected to a mechanical ventilator. In a particularly preferred embodiment, said aerosol delivery end of said positioned catheter extends to i) just before (e.g. within an inch), ii) at or iii) just below (e.g. within an inch) said lower end of said tube (thereby bypassing potential blockages caused by the ventilation tubing). However, in one embodiment, said aerosol delivery end of said positioned catheter is well within the endotracheal tube (positioned in the upper one third or middle one third of the endotracheal tube) such that said aerosol first contacts the endotracheal tube and thereafter contacts the patient's trachea.

In one embodiment, particular with respect to "constant-flow" ventilators, the present invention contemplates limiting the delivery event strictly to the inspiratory phase of the ventilator cycle and, if possible, at a reduced flow-rate. Thus, in one embodiment, said aerosolizing of step (c) is actuated on (or in fixed realtion to) the inspiration phase of the breathing cycle. In one embodiment, a mechanical ventilator controls a breathing cycle for the patient, said cycle comprising an inspiration phase of the breathing cycle.

In another embodiment, delivery is through the catheter is "continuous" and not limited to the inspiratory phase. In one embodiment, a vancomycin/gentamycin formulation is delivered continuously via an aerosol catheter (such as the Trudell catheter).

It is not intended that the present invention be limited to particular dosages. On the other hand, the efficiency of the aerosol systems and methods described herein permit amounts to be delivered that are too low to be generally effective if administered systemically, but are nonetheless effective amounts when administered in a suitable and pharmaceutically acceptable formulation directly to the airway. Importantly, while efficiencies can be increased, in preferred embodiments efficiencies are not increased at the expense of control over the dose. Thus, lower efficiencies are contemplated as preferred when delivery is more reproducible.

It is not intended that the present invention be limited to antimicrobials that only kill particular organisms. The present invention contemplates drugs and drug combinations that will address a wide variety of organisms. In a preferred embodiment, the present invention contemplates drugs or drug combinations effective in the treatment of infections caused by *P. aeruginosa*, *S. aureus*, *H. influenza*, and *S. pneumoniae* and/or antibiotic-resistant strains of bacteria such as methicillin-resistant *S. aureus*, among others.

Of course, antivirals can also be aerosolized and administered in the manner of the antibiotic formulations of the present invention. This is particularly significant given the outbreak of severe acute respiratory syndrome (SARS) in Hong Kong. The symptoms of SARS include fever, chills, myalgia and cough. People of older age, people with lymphopenia, and people with liver dysfunction typically are associated with severe disease. It is believed that the infectious agent is a virus belongin to the family Coronaviridae.

While preferred embodiments of the present invention address infections, the present invention contemplates that the improved aerosol systems and methods can be applied to any patient, human or animal, in need of an aerosol to the trachea and/or deep lung. For this reason, other drugs (e.g. steroids, proteins, peptides, nucleic acids, bronchodilator, surfactant, lidocaine . . . ) are contemplated as aerosols. Moreover other types of patients (e.g. cystic fibrosis, lung cancer, COPH, ARDS, SAID, Heaves, respiratory infections, asthma, bronchospasm) are contemplated.

Moreover, while preferred embodiments of the present invention are presented in the context of the intubated patient, other patients at risk for infection are contemplated as treatable with the methods and devices of the present invention. For example, the elderly (particularly those in nursing homes), horses, dogs and cats in competitions (show and racing animals), animals that frequently travel (e.g. circus animals), animals in close quarters (e.g. zoos or farms), humans and animals in general are at risk for lung infections. The present invention contemplates delivery of aerosols to the trachea and/or deep lung for such individuals—both prophylactically (i.e. before symptoms) and under acute conditions (i.e. after symptoms)—wherein said aerosols comprise antimicrobials, and in particular, the antibiotic mixtures described above.

In one embodiment, the present invention contemplates administering the appropriate medication to a patient diagnosed with ARDS or chronic obstructive pulmonary disease (COPD). This invention contemplates an embodiment of a method, comprising: a) providing: i) a patient (whether human or animal) exhibiting one or more symptoms of ARDS (or simply a patient who, because of prior diagnosis with chronic or acute conditions of AIDS, tuberculosis, flu, emphysema, cystic fibrosis, heaves, is either currently infected or at risk for infection, or who exhibits increases in mucus or sputum), ii) a formulation of the appropriate medication, and iii) an aerosol delivery catheter comprising an upper end and a lower end, said lower end comprising an aerosol delivery end; b) inserting said aerosol delivery end of said catheter into said patient's trachea to create a positioned catheter (if the patient has an intubation tube the catheter is configured to fit inside or along side said tube); and c) aerosolizing said formulation under conditions such that said formulation is delivered through said positioned catheter to said patient.

The present invention is not limited to any precise desired outcome when using the above-described compositions, devices and methods. However, it is believed that the compositions, devices and methods of the present invention may result in a reduction in mortality rates of intubated patients, a decrease in the incidence of resistance (or at least no increase in resistance) because of the reduced systemic antibiotic exposure and elevated exposure at the targeted mucosal surface of the lung caused by local administration. As noted above, it is contemplated that the compositions, devices and methods of the present invention are useful in the treatment of pneumonia (and may be more effective than systemic treatment—or at the very least, a useful adjunct). It is believed that related infections may also be prevented or reduced (e.g. prevention of sepsis, suppression of urinary tract infections, etc.)

Of course, a reduced use of systemic antibiotics because of the efficacy of the compositions, devices and methods of the present invention may result in reduced cost, reduced time on IV lines, and/or reduced time on central lines). Moreover, such a reduction should reduce antibiotic toxicity (as measured by reduced incidence of diarrhea and *C. difficile* infection, better nutrition, etc.)

It is believed that the compositions, devices and methods of the present invention will locally result in a reduction of the ET/Trach tube biofilm. This should, in turn, get rid of secretions, decrease airway resistance, and/or decrease the work of breathing. The latter should ease the process of weaning the patient off of the ventilator The present invention contemplates specific embodiments that can replace commonly used elements of a ventilator system. In one embodiment, the present invention contemplates a modular Y piece attachable to a ventilator and to an endotracheal tube, wherein the lower arm of the Y piece comprises an aerosol generator. While not limited to any precise desired outcome, it is contemplated that the modular Y piece with integral generator will reduce the effects of the ventilator on all conventional aerosol systems (jet, ultrasonic and MDI), and at the same time enhance the positive qualities of a device like the Aerogen™ pro. Again, While not limited to any precise desired outcome, it is contemplated that the modular Y piece with integral generator will: (1) reduce variability in delivery (reduced effects of humidification, bias flow, continuous vs breath-actuated) so as to achieve the same delivery (no matter what commercial ventilator system is used); (2) allow for maximal effects of breath actuation; and (3) allow for maximal effect to enhanced nebulizer efficiency using nebulizers having no dead volume.

In one embodiment, the present invention contemplates a method, comprising: a) providing: i) a patient, said patient intubated with a tube selected from endotracheal tubes and tracheostomy tubes (whether or not said patient is exhibiting signs of infection), said tube having a lower end and an upper end; ii) a formulation comprising a first antibiotic; iii) a aerosol delivery device comprising an upper end and a lower end, said lower end comprising an aerosol delivery end configured to fit within said patient's trachea; b) inserting said aerosol delivery end of said device within said patient's trachea to create a positioned device; and c) aerosolizing said formulation under conditions such that said formulation is delivered through said aerosol delivery end of said positioned device to said patient, wherein said aerosol first contacts said trachea. In one embodiment, said aerosol delivery device comprises an aerosol delivery catheter. In another embodiment, said aerosol delivery device comprises a bronchoscope fitted with an aerosolizing nozzle. In yet another embodiment, said aerosol delivery device comprises a metered dose inhaler fitted with a nozzle extension.

While the present invention is not limited to the nature of the formulation, in one embodiment, said formulation further comprises a second antibiotic, wherein said first antibiotic has activity against gram positive bacteria and said second antibiotic has activity against gram negative bacteria. In yet another embodiment, the formulation further comprises a bronchodilator (e.g. albuterol).

In one embodiment, the present invention contemplates a method, comprising: a) providing: i) an intubated patient exhibiting one or more symptoms of microbial infection, ii) a formulation comprising a first antibiotic having activity against gram positive bacteria and a second antibiotic having activity against gram negative bacteria; iii) a aerosol delivery catheter comprising an upper end and a lower end, said lower end comprising an aerosol delivery end configured to fit within said tube; b) inserting said aerosol delivery end of said catheter within said tube to create a positioned catheter; and c) aerosolizing said formulation under conditions such that said formulation is delivered through said positioned catheter to said patient. Over time, it is contemplated that such administration will reduce (but need not eliminate completely) one or more of said symptoms. For example, such administration may reduce the CPIS score (discussed in more detail below) or may reduce one or more factors used to calculate the CPIS score. On the other hand, such administration may reduce the amount of secretions (e.g. sputum) in a defined time period.

While the present invention is not limited to any precise configuration, it is contemplated that the above-described method is performed in the context where said tube is connected to a mechanical ventilator. While the present invention is not limited to the precising timing of delivery, in one embodiment said mechanical ventilator controls a breathing cycle, said cycle comprising an inspiration phase of the breathing cycle and said aerosolizing of step (c) is actuated on the inspiration phase of the breathing cycle.

The present invention is not limited to any precise positioning of the catheter, In one embodiment, said aerosol delivery end of said positioned catheter extends i) just before (e.g. within 3 cm), ii) at, or iii) just below (e.g. with 3 cm) of said lower end of said tube. However, in one embodiment, said aerosol delivery end of said positioned catheter is well within the endotracheal tube (positioned in the upper one third or middle one third of the endotracheal tube) such that said aerosol first contacts the endotracheal tube and thereafter contacts the patient's trachea.

In yet another embodiment, the present invention contemplates a method, comprising: a) providing: i) a patient exhibiting an elevated white blood cell count (and/or an elevated CPIS score); ii) a formulation comprising a first antibiotic having activity against gram positive bacteria and (optionally) a second antibiotic having activity against gram negative bacteria; iii) a aerosol delivery device comprising an upper end and a lower end, said lower end comprising an aerosol delivery end configured to fit within said patient's trachea; b) inserting said aerosol delivery end of said device within said patient's trachea to create a positioned device; and c) aerosolizing said formulation under conditions such that said formulation is delivered through said aerosol delivery end of said positioned device to said patient to create a treated patient, wherein said aerosol first contacts said trachea. Over time, it is contemplated that such administration will reduce the white blood cell count (in some cases to a number in the normal range). Therefore, in one embodiment, the method further comprises d) measuring the white blood cell count of said treated patient after step (c).

However, white blood cell count is only one of a number of indicators. By way of example, such administration may reduce the CPIS score [e.g. from 6 (or >6) to 4 or less] or may reduce one or more factors used to calculate the CPIS score. On the other hand, such administration may reduce the amount of secretions (e.g. sputum) in a defined time period.

Again, while the present invention is not limited to any precise configuration, it is contemplated that the above-described method is performed in the context where said tube is connected to a mechanical ventilator. While the present invention is not limited to the precising timing of delivery, in one embodiment said mechanical ventilator controls a breathing cycle, said cycle comprising an inspiration phase of the breathing cycle and said aerosolizing of step (c) is actuated on the inspiration phase of the breathing cycle.

Again, the present invention is not limited to any precise positioning of the catheter, In one embodiment, said aerosol delivery end of said positioned catheter extends i) just before (e.g. within 3 cm), ii) at, or iii) just below (e.g. with 3 cm) of said lower end of said tube.

The present invention also contemplates devices and formulations (independent of how they are used). While the present invention is not limited to the nature of the formulation, in one embodiment, said formulation further comprises a first antibiotic with activity against gram positive bacteria and a second antibiotic with activity against gram negative bacteria. In yet another embodiment, the formulation further comprises a bronchodilator (e.g. albuterol). In one embodiment, a single antibiotic is used together with a bronchodilator. It has been found that this combination is useful due to the observation (in some cases) of a post-antibiotic bronchospasm when antibiotic is used alone.

In one embodiment, the present invention contemplates a device, comprising a fluid driving element attached to a dose metering element, said dose metering element engaged (directly or indirectly through other elements) to an aerosolizing catheter, said catheter comprising an aerosol delivery end. In a preferred embodiment, said dose metering element is detachably engaged (e.g. screw mounted, snap mounted, slide mounted and held by virtue of the fact that the tubing slides over or slides within other tubing) to said aerosolizing catheter. In one embodiment, said dose metering element comprises a reservoir of defined volume. In one embodiment, said reservoir is loaded with a drug formulation (e.g. an antibiotic formulation). In one embodiment, said reservoir is configured as a transparent or semi-transparent cylinder. In one embodiment, said cylinder comprises visible measurement indicia. In one embodiment, said fluid driving element comprises a plunger driven by compressed gas, said compressed gas stored in a canister. In one embodiment, said aerosolizing catheter is of such dimensions such that it can to fit inside an endotracheal tube. In one embodiment, said delivery end of said aerosolizing catheter comprises a baffle.

In one embodiment, the present invention also contemplates a device comprising tubing configured approximately as a Y piece, said device having a first end attachable to a ventilator and a second end attachable to an endotracheal tube, wherein said second end comprises an aerosol generator. In one embodiment, said aerosol generator is integral to said second end (e.g. attached at the time of molding the piece). In one embodiment, said aerosol generator is drug-loaded.

In another embodiment, the present invention contemplates a system comprising a ventilator circuit, said circuit comprising i) an inspiratory line and an expiratory line converging at a junction, ii) a nebulizer positioned in proximity to said junction and in fluid communication with an endotracheal tube (or tracheostomy tube), wherein said nebulizer is not positioned in said inspiratory line or said expiratory line. The nebulizer is positioned "in proximity" to said junction when it is placed between said junction and said endotracheal tube (and optionally, it can be placed so that it is closer to said junction than it is to said endotracheal tube).

It is not intended that the present invention be limited to the precise configuration of the junction. In one embodiment, said junction comprises a Y piece (or "T" piece, or "V" piece) having a first end, a second end, and a stem (the "V" piece stem is just the bottom point of the "V"). It is preferred in this embodiment that said inspiratory line is attached to said first end of said Y piece, and wherein said expiratory line is attached to said second end of said Y piece. In one embodiment, said nebulizer is positioned in said stem of said Y piece. In one embodiment, said nebulizer is simply attached to said stem of said Y piece. In a preferred embodiment, a nebulizer adapter is inserted between the Y piece and the endotracheal tube such that said nebulizer can be positioned (i.e. the nebulizer fits into the adapter in a male-female manner, as a snap fit, etc). In yet another embodiment, said nebulizer is integral to said stem of said Y piece.

The present invention is not limited to the precise configuration or nature of the circuit. In one embodiment, said circuit is a closed circuit. In another embodiment, said circuit is an open circuit.

The present invention also contemplates an embodiment of a device comprising tubing configured approximately as a Y piece (or "T" piece, or "V" piece), said device comprising i) a first end attachable to an inspiratory line of a ventilator circuit, ii) a second end attachable to an expiratory line of a ventilator circuit, and iii) a stem comprising an nebulizer. In one embodiment, said nebulizer is positioned in said stem of said Y piece. In one embodiment, said nebulizer is simply directly or indirectly (e.g. via another tube or suitable element) attached to said stem of said Y piece. In a preferred embodiment, a nebulizer adapter is inserted between the Y piece and the endotracheal tube such that said nebulizer can be positioned (i.e. the nebulizer fits into the adapter in a male-female manner, as a snap fit, etc). In yet another embodiment, said nebulizer is integral to said stem of said Y piece. The nebulizer can either be empty (loaded later) or drug-loaded (provided to the end user in a loaded form).

While not limited to how the above devices are used, in one embodiment the present invention contemplates a method comprising a) providing a subject attached to a ventilator circuit via a tube selected from an endotracheal tube and a tracheostomy tube, said ventilator circuit comprising i) an inspiratory line and an expiratory line converging at a junction, ii) a nebulizer positioned in proximity to said junction and in fluid communication with said tube, wherein said nebulizer is not positioned in said inspiratory line or said expiratory line; b) administering aerosolized antibiotic to said subject via said nebulizer. The subject might be a human or animal. In one embodiment, said subject is a patient exhibiting one or more symptoms of infection. In one embodiment, said nebulizer, prior to step (b) contains an antibiotic formulation. In one embodiment, said antibiotic formulation comprises a first antibiotic having activity against gram positive bacteria and a second antibiotic having activity against gram negative bacteria.

In another embodiment, the present invention contemplates a method, comprising a) providing a patient exhibiting one or more symptoms of microbial infection, said patient intubated with a tube selected from endotracheal tubes and tracheostomy tubes, said tube connected to a ventilator circuit comprising i) an inspiratory line and an expiratory line converging at a junction, ii) a nebulizer positioned in proximity to said junction and in fluid communication with said tube, wherein said nebulizer is not positioned in said inspiratory line or said expiratory line, and wherein said nebulizer contains a formulation comprising two or more antibiotics; b) administering said formulation as an aerosol to said patient via said nebulizer. While not limited to the precise formulation, in one embodiment said formulation comprises a first antibiotic having activity against gram positive bacteria and a second antibiotic having activity against gram negative bacteria.

Again, the present invention is not limited to particular vent configurations. In one embodiment, said inspiratory and said expiratory lines are connected to a mechanical ventilator. In one embodiment, said mechanical ventilator controls a breathing cycle, said cycle comprising an inspiration phase. In one embodiment, said administering of said aerosol of step (b) is actuated on the inspiration phase of the breathing cycle.

Again, the present invention is not limited to particular vent features or modes of operation. In one embodiment, said mechanical ventilator comprises a humidifying element. In one embodiment, said administering of said aerosol of step (b) is actuated when said humidifying element is not active.

DESCRIPTION OF THE DRAWINGS

FIG. 16 shows a bench model wherein the proximal airways (and deposition therein) are modeled. In FIG. 16A, the aerosol generator is a nebulizer. In FIG. 16B, the aerosol generator is an aerosol catheter.

FIG. 17 shows various embodiments of a device for attaching a nebulizer to a ventilator circuit.

DEFINITIONS

An "aerosol" is herein defined as a suspension of liquid or solid particles of a substance (or substances) in a gas. The term "charge" is used to describe the amount of drug placed into the delivery system. "Inhaled mass" refers to the actual amount inhaled by the patient. "Deposition" refers to the dose actually deposited in the patient. With respect to delivering aerosols according to the various embodiments of the present invention, it is preferred that the "deposition" of antibiotics is always lower than the systemic dose currently used. On the other hand, the "charge" may be high depending on device efficiency. Importantly, even with low efficiency delivery, good control over delivery (reproducible over a small range) is preferred as the means of controlling dose.

The present invention contemplates the use of both atomizers and nebulizers of various types. An "atomizer" is an aerosol generator without a baffle, whereas a "nebulizer" uses a baffle to produce smaller particles. However, the term "nebulizer" in the claims is meant to encompass atomizers.

In one embodiment, the present invention contemplates using the commercially available Aerogen™ aerosol generator which comprises a vibrational element and dome-shaped aperture plate with tapered holes. When the plate vibrates several thousand times per second, a micro-pumping action causes liquid to be drawn through the tapered holes, creating a low-velocity aerosol with a precisely defined range of droplet sizes. The Aerogen™ aerosol generator does not require propellant.

Figure 6:
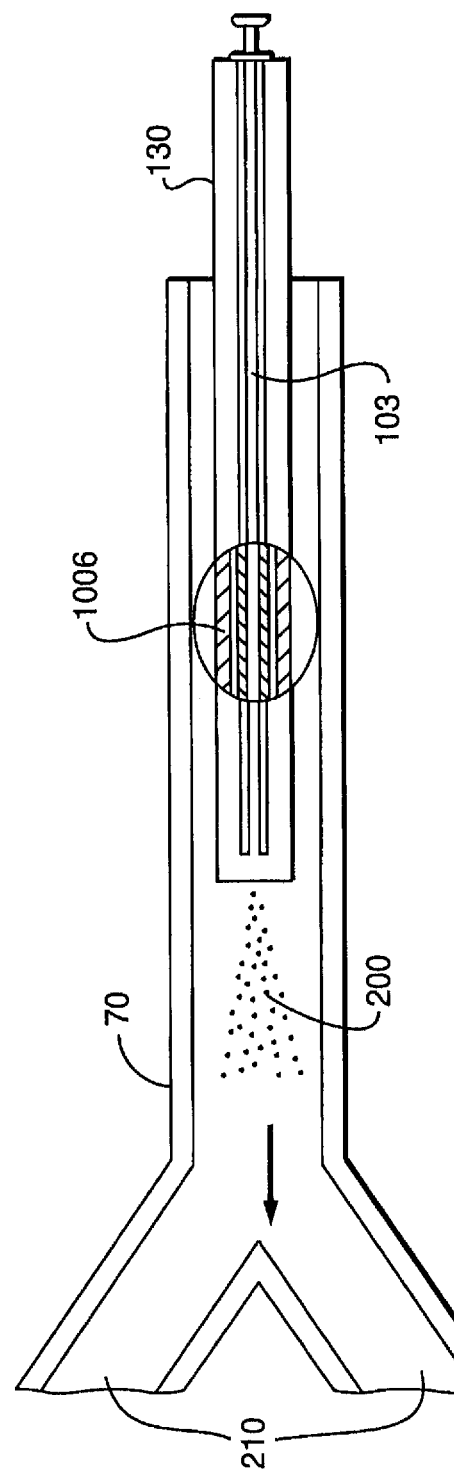
FIG. 6 is a diagram of an aerosol catheter and a suction catheter in operative combination.

"Baffling" is the interruption of forward motion by an object, i.e. by a "baffle." Baffling can be achieved by having the aerosol hit the sides of the container or tubing. More typically, a structure (such as a ball or other barrier) is put in the path of the aerosol (See e.g. U.S. Pat. No. 5,642,730, hereby incorporated by reference, and in particular FIG. 6, element 6). The present invention contemplates the use of a baffle in order to slow the speed of the aerosol as it exits the delivery device.

A "dose metering element" is an element that controls the amount of drug administered. The element can, but need not, measure the amount of drug as it is administered. In a preferred embodiment, the element is characterized simply as a container of defined volume (e.g. a reservoir). In a preferred embodiment, the defined volume is filled by the manufacturer or hospital professional (e.g. nurse, pharmacist, doctor, etc.) and the entire volume is administered. In another embodiment, the reservoir is configured as a transparent or semi-transparent cylinder with visible measurement indicia (e.g. markings, numbers, etc.) and the filling is done to a desired point (e.g. less than the entire capacity) using the indicia as a guide.

A "fluid driving element" is an element that moves fluid in a direction along the device. In simple embodiments, the fluid driving element comprises a plunger driven by compressed gas, said compressed gas stored in a canister. In other embodiments, it comprises a pump. In still other embodiments, it comprises a hand actuated plunger (in the manner of a syringe).

One element is in "fluid communication" or "fluidic communication" with another element when it is attached through a channel, tube or other conduit that permits the passage of gas, vapor and the like. Indeed, the tubing associated with commercially available ventilators creates a "circuit" for gas flow by maintaining fluidic communication between the elements of the circuit. Ports in the circuit allow for the circuit to be temporarily open so that devices and drugs can be introduced. "Tubing" can be made of a variety of materials, including put not limited to various plastics, metals and composites. Tubing can be rigid or flexible. Tubing can be "attached" in a detachable mode or a fixed mode. Tubing is typically attached by sliding into or over (both of which are examples of "slidably engaging") other tubing or connectors.

A "patient" is a human or animal and need not be hospitalized. For example, out-patients, persons in nursing homes are "patients."

A "patient exhibiting one or more symptoms of microbial infection" may have fever or other traditional symptoms, or may exhibit increase secretions, organisms in the BALF, or other symptoms. A "patient at risk for infections" includes, but is not limited to, trauma patients, intensive care patients, intubated patients, elderly patients, low birth weight patients and immunocompromised patients.

A "positioned" device is positioned in vivo, i.e. in the context of the patient. For example, in certain embodiments, it is desired that an aerosol catheter is positioned such that the aerosol first contacts the trachea. In another embodiment, the aerosol first contacts the endotracheal tube. In another embodiment, the aerosol is simply brought in contact with the "biofilm" associated with the infection, whether or not the biofilm extends beyond the trachea.

"Jet nebulizers" draw up liquid by capillary action such that the liquid reaches a jet stream, is drawn into the jet stream, and is shattered into small particles.

"Ultrasonic nebulizers" use electric current to produce sound waves that break up liquid into an aerosol. An ultrasonic nebulizer includes a ceramic transducer (including piezo electronic technology) that changes electrical energy into pressure energy. The transducer vibrates at a very high frequency of up to about 1.5 mHz. The vibrational energy is transmitted through water and focused on a flexible diaphragm that vibrates. The diaphragm is in contact with the solution to be aerosolized and shakes the solution into particles. At high frequencies a fine mist is generated. Ultrasonic nebulizers may produce a more consistent particle size than do jet nebulizers and may produce very large volumes of respirable particles with much greater deposition into the lungs.

The present invention contemplates in some embodiments utilizing nebulizers and aerosol drug delivery devices based upon piezo electronic technology (e.g. Pari GmBh (Sternberg, Germany) e-Flow™ electronic nebulizers based on piezo ceramic electronic transducers), including portable nebulizers and aerosol devices (e.g. Omron Healthcare, Inc Portable Ultrasonic Nebulizer, NE-UO3V MicroAir) and inhaled drug delivery technology (e.g. Mystic™ drug inhalation technology BattellePharma).

"Acute Respiratory distress syndrome" (ARDS) is a sudden, life threatening lung failure from inflamed alveoli that fill with liquid. It is often treated by mechanical ventilation with antibiotics.

Airflow Obstruction (see Heaves (COPD), and SAID).

Bronchodilator An inhaled short-acting aerosol medication typically used to provide immediate relief by rapidly opening up the airways.

SAID (Small Airway Inflammatory Disease) A disease of the lower airways causing cough and exercise intolerance in horses. This is less severe than Heaves.

Heaves (Chronic Obstructive Pulmonary Disease or Chronic Obstructive Lung Disease) is characterized by forced expiratory effort due to the narrowing of the small airways of the lungs. This condition is also known as chronic obstructive pulmonary disease (COPD).

pMDI (pressurized Metered Dose Inhaler) (also referred to as MDI or Metered Dose Inhaler) This device creates an aerosol upon depressing the canister. Each time the canister is depressed a single dose of medication is dispensed.

Wet Nebulizer (also known as jet nebulizer) A wet nebulizer works by directing a high flow of gas against a liquid drug in order to produce a mist of tiny droplets or particles.

Further embodiments include drug formulations and combinations of topical anethetics and disease or condition specific antibiotics (e.g. aerosolized lidocaine and Corus 1020 antibiotic (Corns Pharma Inc.)).

An example of a "dry powder" formulation is formoterol fumerate inhalation powder for asthma and prevention, of bronchospasm (Novartis).

Description of The Invention

Defining The Patient's Condition. While the association of infection with mechanical ventilation is clear, the precise nature of the disease (that either causes or is the result of the infection) is not. "Pneumonia" is not a well-defined condition. The so-called "gold standard" for diagnosing pneumonia is histological examination (typically done post mortem). However, recognition of histologic pneumonia varies among pathologists. Using a. study group consisting of 39 patients who died after a mean of 14 days of mechanical ventilation, a panel of pathologists did not agree on the diagnosis. Indeed, when the same slides were examined 6 months later by the same panel, some of the patients were re-classified. Corley D. E. et al, "Reproducibility of the Histologic Diagnosis of Pneumonia Among a Panel of Four Pathologists" Chest 112:458 (1997). On the other hand, using the same study group, it was shown that a bronchoaveolar lavage fluid (BALF) with a cell population comprising <50% neutrophils had a 100% negative predictive value for histologic pneumonia. In some embodiments, the present invention utilizes this BALF measurement as a means of excluding pneumonia/infection in the ventilated patient. In some embodiments, VAPis confirmed by the presence of at least two of the following criteria: >or =2% of cells in BALF contain intracellular bacteria found on direct examination of BALF; protected-specimen brush sample culture with >or =$10^3$ cfu/ml; or BALF culture with >or =$10^4$ cfu/ml. See Combes A. et al., "Incidence and outcome of polymicrobial ventilator-associated pneumonia" Chest 121-1618 (2002).

While the general literature describes infections in the context of the intubated patient under the general label "VAP" (for ventilator-associated pneumonia), the present inventors recognize that such patients at least initially develop a more limited or localized disease best described as "tracheobronchitis." While not intending to limit the invention in any manner to a particular disease mechanism, it is believed that tracheobronchitis develops at or around the endotracheal tube (particularly at or near the place where the tube is "anchored" with a cuff, e.g. balloon cuff, or at or near the end of the tube) due to invasion into the proximal airway by the mixed flora of the oro-pharynx. In other words, the tube brings the flora of the oro-pharynx down into the trachea, where it grows at the initial site of infection. Other hydrophilic organisms such as *Pseudomonas* may bypass the oropharynx and colonize the trachea directly using the endotracheal tube or tracheostomy tube as a conduit.

While it is not intended that the present invention be limited to a theory of how disease progresses in the intubated patient, it is believed that one can delay or even prevent pneumonia by treating (or preventing) tracheobronchitis according to the methods and devices of the present invention. The present invention contemplates that diagnosis of tracheobronchitis can be readily done by measurement of sputum levels.

Figure 1B:
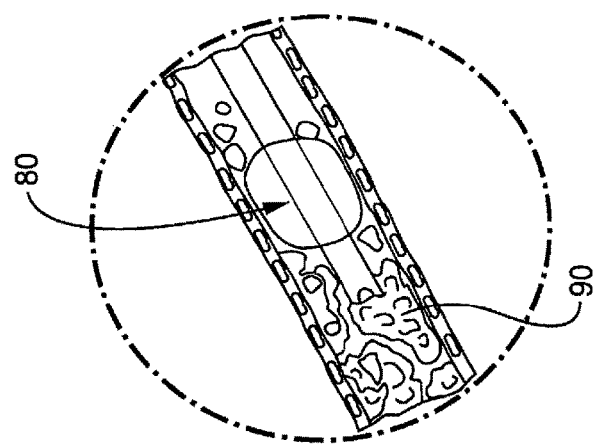
FIG. 1B is a magnified view of the circled area of FIG. 1A
Figure 1A:
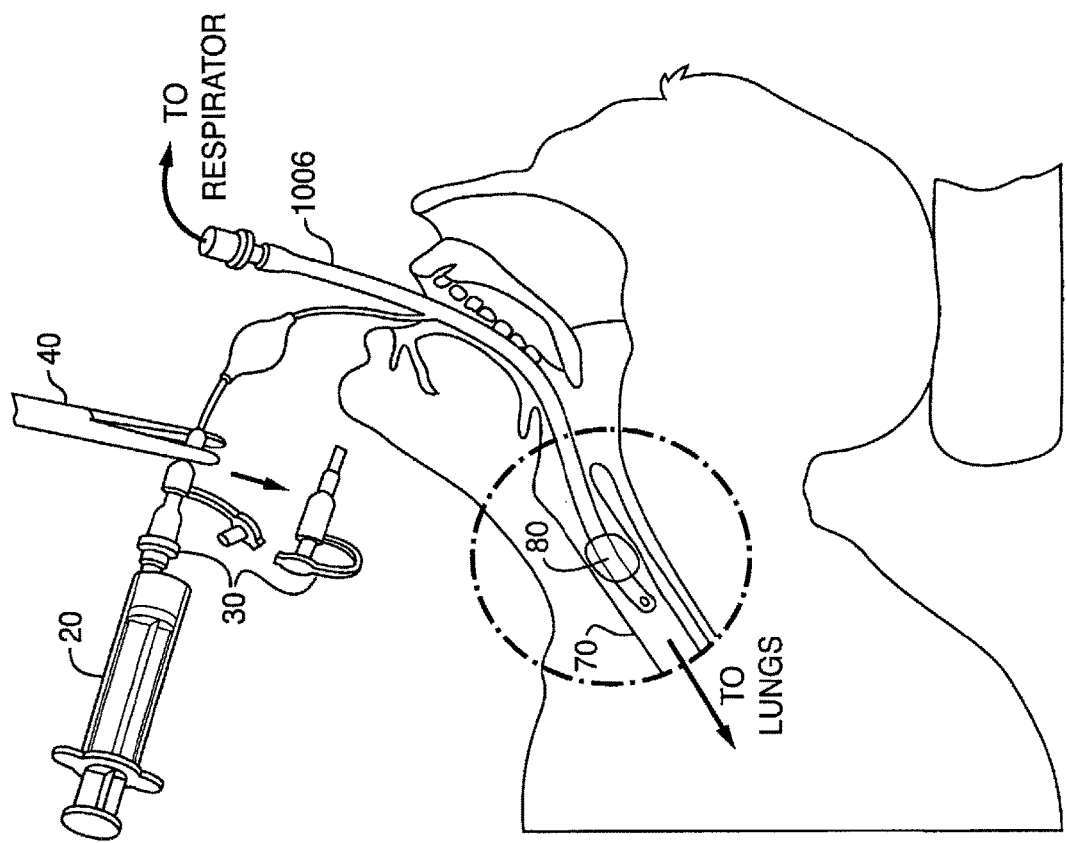
FIG. 1A is a diagram of a conventional endotracheal intubation.
Figure 2A:
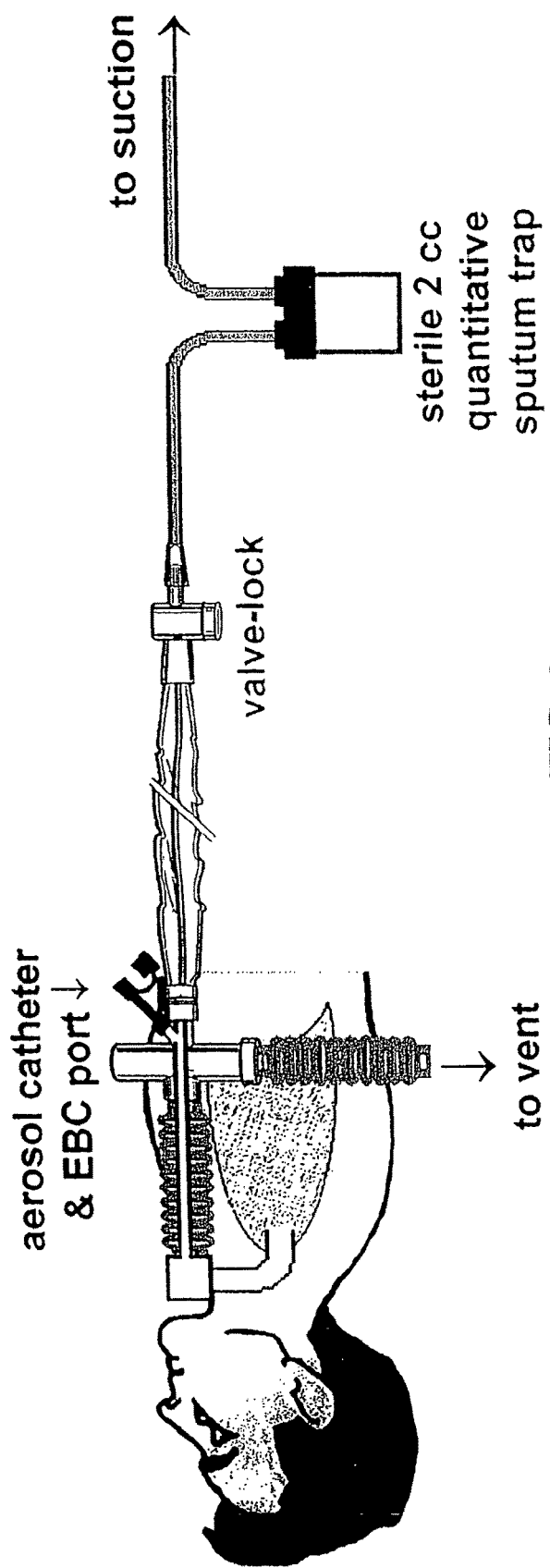
FIG. 2A is a diagram of a patient with a tracheostomy tube and an inline sputum trap (i.e. as part of the ventilation system).
Figure 2B:
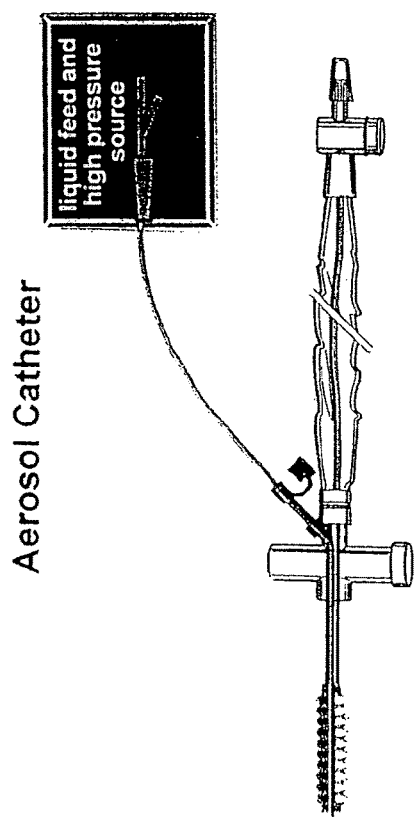
FIG. 2B shows the engagement of an aerosol catheter with a port in the ventilation system.
Figure 2C:
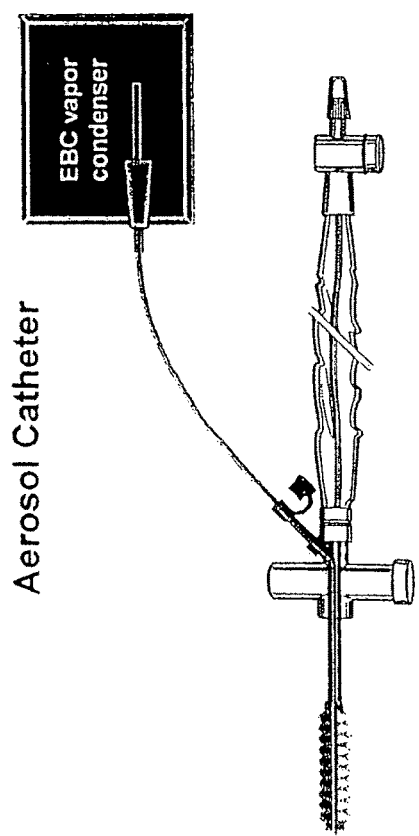
FIG. 2C shows the engagement of an EBC system with a port in the ventilation system.
Figure 3:
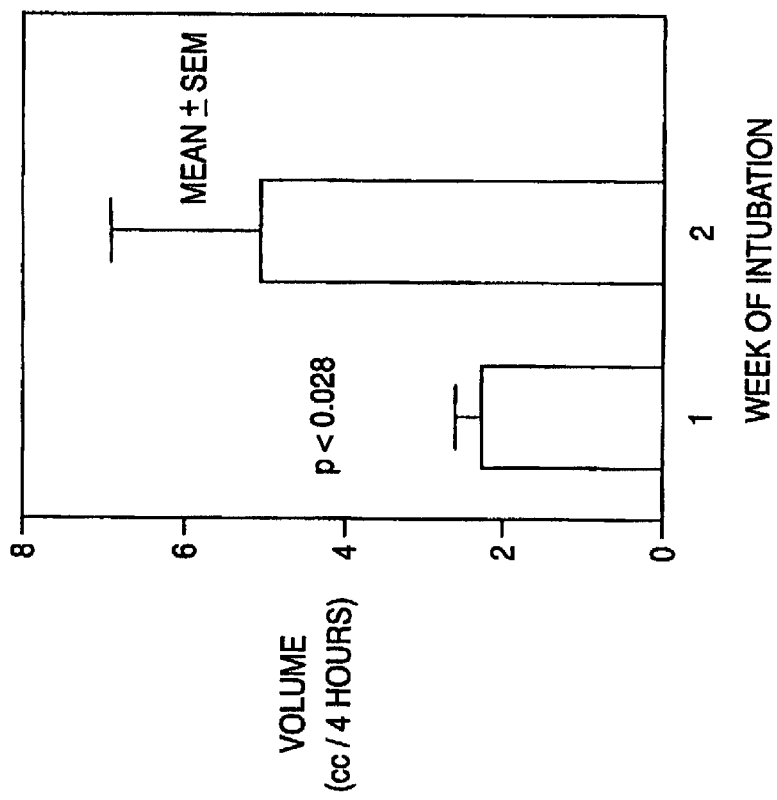
FIG. 3 is a bar graph showing the increase in sputum measured in the sputum trap of FIG. 2 as a function of weeks of intubation.

By way of illustration, FIG. 1A is a diagram of a conventional endotracheal intubation. FIG. 1B is a magnified view of the circled portion of FIG. 1A showing the balloon cuff that anchors the endotracheal tube and schematically shows the local area of infection characteristic of tracheobronchitis. FIG. 2 is a diagram of a patient with a tracheostomy tube system with an inline sputum trap. FIG. 3 is a bar graph showing the increase in sputum measured in the sputum trap of FIG. 2 as a function of weeks of intubation.

The data of FIG. 3 justifies two alternative approaches to therapy, both of which are contemplated by the present invention. In one embodiment, the present invention contemplates prophylactic aerosols of antibiotic mixtures to the trachea and/or deep lung after approximately seven (7) days of intubation (or after no fewer than 3 days of intubation and no less than approximately 7 days of intubation)-regardless of whether symptoms of infection are detectable. In another embodiment, a diagnosis of tracheobronchitis is made where the volume of secretions (e.g. sputum levels) exceed approximately 2 cc in any 4 hour measurement period (regardless of the number of days of intubation).

Figure 4:
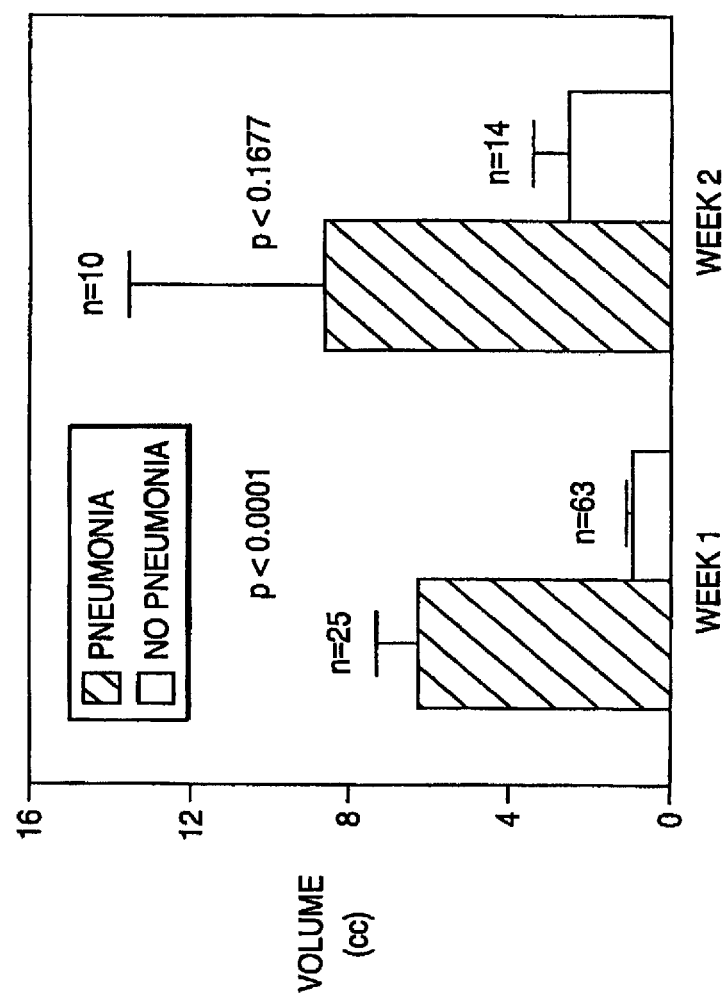
FIG. 4 is a bar graph showing the relationship of high sputum levels to pneumonia (e.g. VAP).
Figure 5:
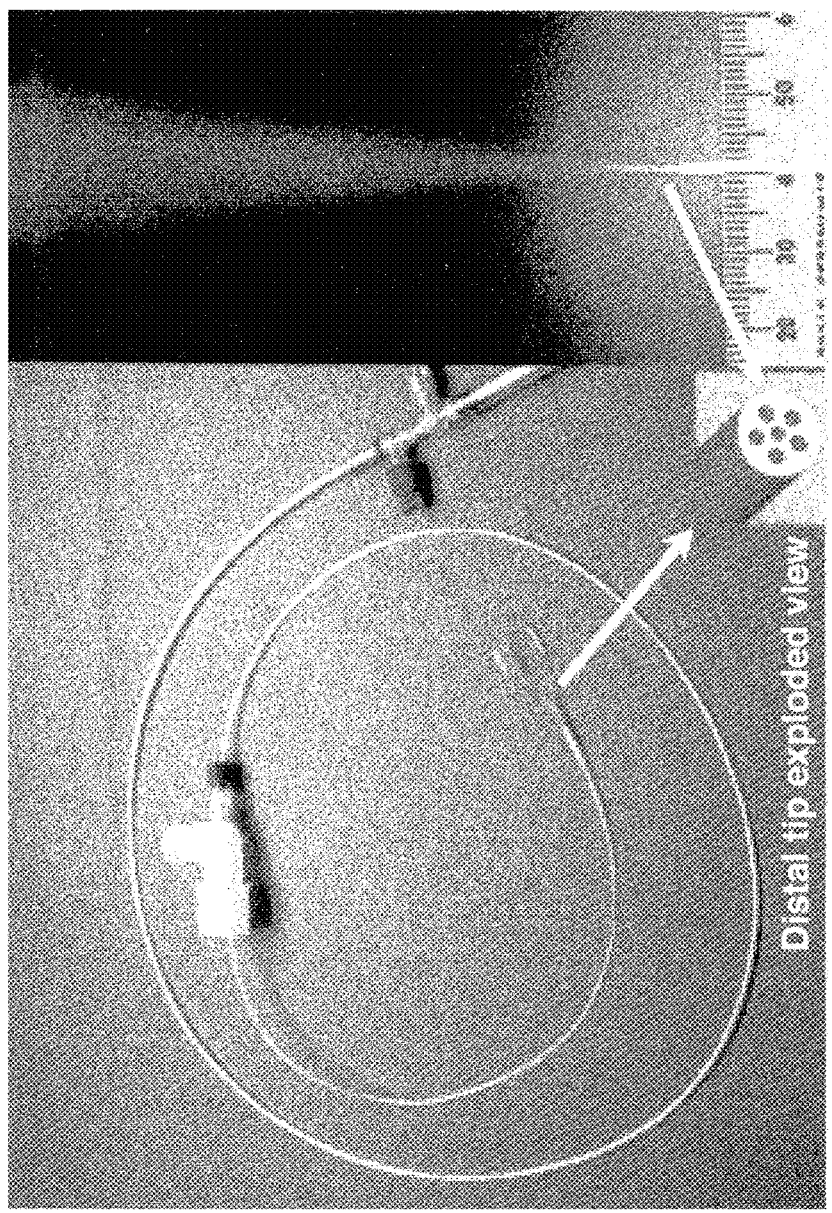
FIG. 5 is a photograph of an exemplary aerosol catheter.

FIG. 4 is a bar graph showing the relationship of high sputum levels to pneumonia (e.g. VAP). While the invention is not limited to any theory of disease progression, the very high sputum levels (greater than approximately 6 cc in any 4 hour measurement period) indicates that the tracheobronchitis has matured into pneumonia, whereas the "no pneumonia" population is believed to have the more localized tracheobronchitis.

Treating Without Testing. In one embodiment, the intubated patients are viewed as "at risk" and the administration of aerosolized antibiotics is prophylactic. In this embodiment, no testing for infection is done. Rather, justification for treatment is provided by the many studies that indicate that the incidence of infection increases with the time intubated. In one embodiment, treatment is done after a certain number of days on a ventilator (e.g. on day three, more preferrably greater than three days, still more preferrably, greater than five days, and more commonly, greater than seven days).

Patient Testing. It is not intended that the present invention be limited to timing or nature of testing. For example, in one embodiment, the present invention contemplates monitoring an intubated patient (e.g. for sputum levels, for bacteria in BALF, etc.) prior to the onset of symptoms of infection. In another embodiment, the present invention contemplates testing for organisms after symptoms are apparent (e.g. fever, congestion, etc.). The standard symptoms making up the "clinical pulmonary infection score" can be used in conjunction with the present invention:

(1) body temperature
(2) white blood cell count
(3) nature of tracheal secretions
(4) oxygenation and ARDS
(5) chest X-ray findings
(6) results of Gram stain and culture of tracheal secretions In a preferred embodiment, intubated patients are tested (e.g. for sputum levels, for bacteria in BALF, and/or white blood cell count, etc.) as a function of the number of intubation days. For example, testing is done just prior and/or just after intubation to obtain a baseline for later comparison. Thereafter, similar testing is done on each intubation day thereafter to obtain relative numbers. In this embodiment, diagnosis of infection is made by showing an increase (e.g. an increase in sputum levels, an increase in bacteria in BALF, and/or increase white blood cell count, etc.) over time—not just by the use of absolute cut-off levels. Of course, cut-off levels can also be used. For example, the typical cut-off for the white blood cell count is 10,000-below which is normal. In one embodiment, intubated patients with a white blood cell count of 10,000 or more (i.e. an "elevated" WBC count) are selected for aerosolized drug administration in the manner described herein.

Figure 7:
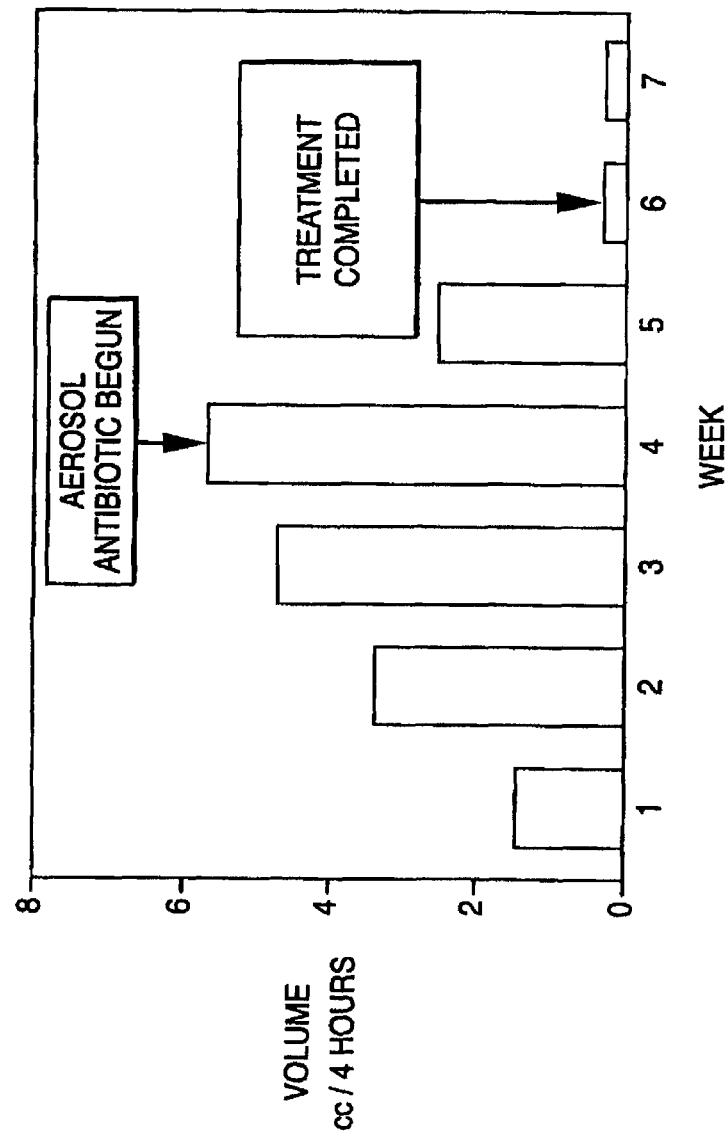
FIG. 7 is a bar graph with data which demonstrates the efficacy of aerosol antibiotic delivered according to the invention as a function of sputum volume, which is a determinant of disease.
Figure 13:
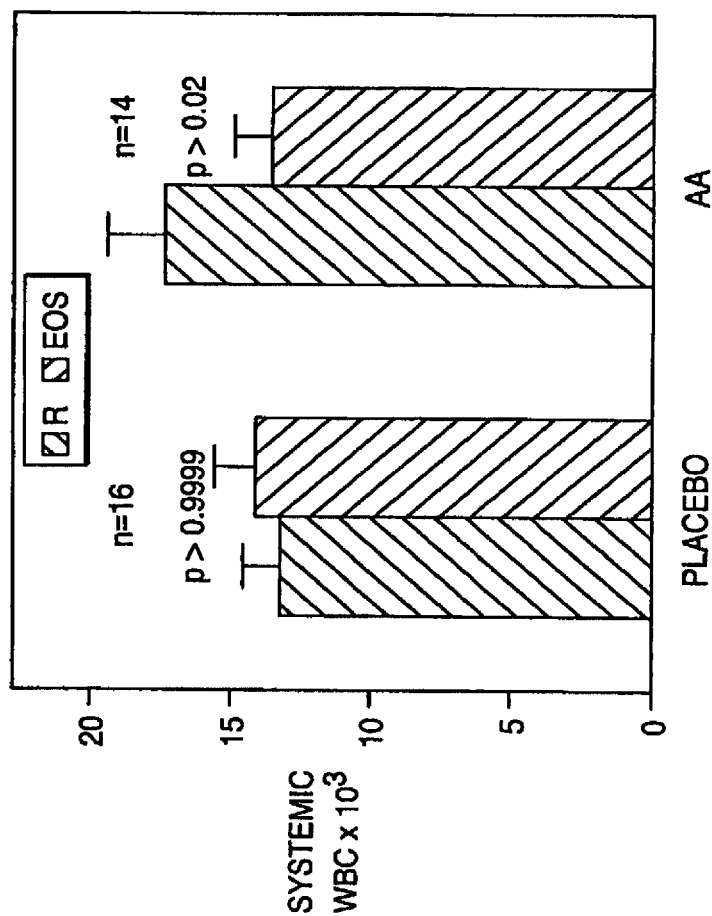
FIG. 13 is a bar graph showing a reduction in white blood cell count following the administration of aerosolized antibiotic.

The present invention also contemplates testing post-treatment (see FIG. 7). That is to say, after aerosolized drug is administered, levels (e.g. sputum levels, bacteria levels in BALF, and/or white blood cell count, etc.) are measured to reveal whether the medication is having the desired impact. For example, in patients with elevated white blood cell counts, a decrease over time (such as a week, but more preferably, within 72 hours, and still more preferably, within 48 hours or less) in white blood cell counts of 10% (more preferably 20% or more) is an indication that the aerosolized drug treatment is having the desired outcome. Such a decrease is shown in FIG. 13, wherein a number ("n") of antibiotic (either gentamicin, amikacin, or vancomycin) treated ("AA") and saline control ("Placebo") patients were tested for their white blood count at the beginning or time of randomization ("R") and at the end of the study ("EOS").

Figure 10:
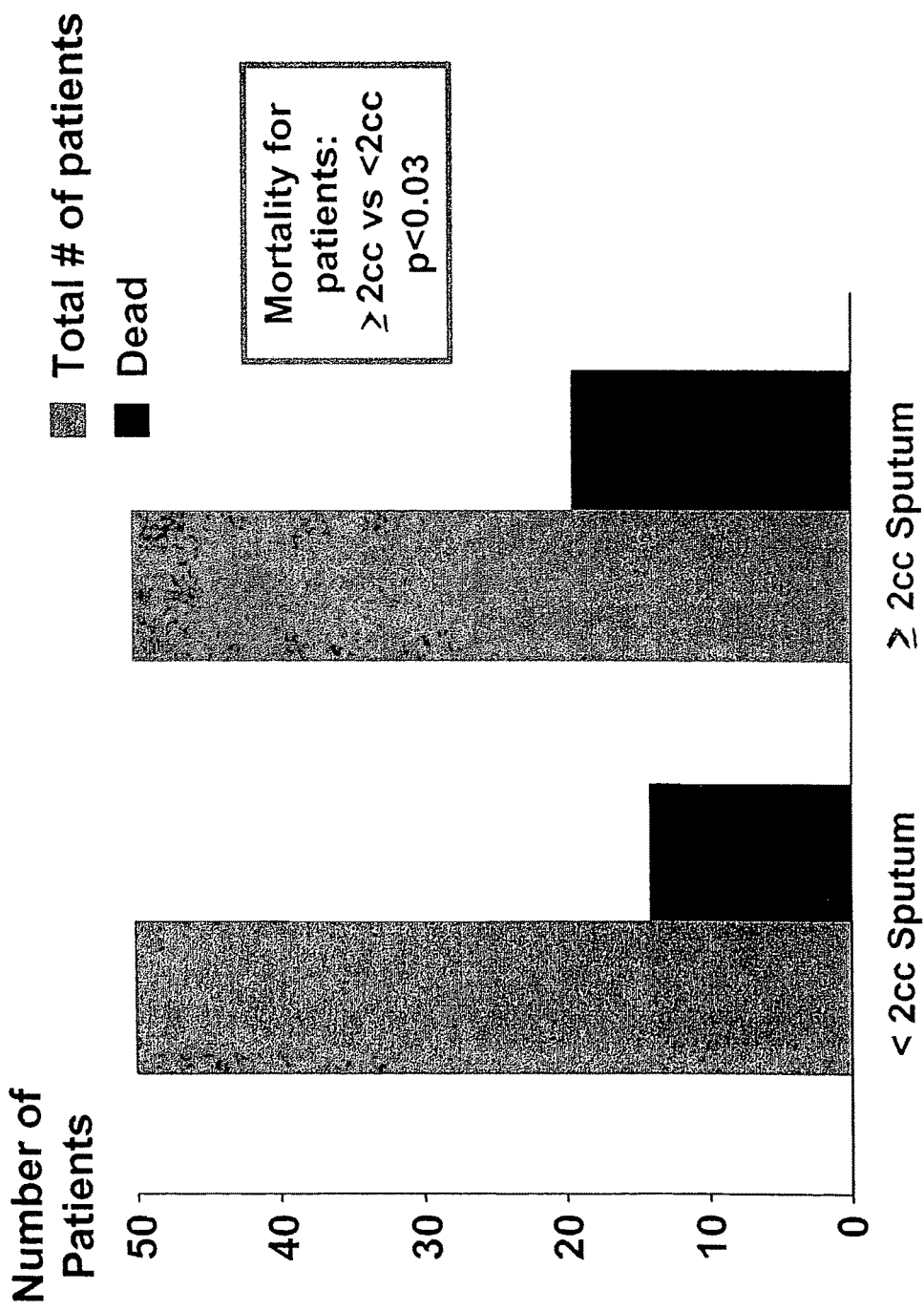
FIG. 10 is a bar graph with mortality data associated with sputum levels exceeding 2 cc in a four hour period.

In one embodiment, the present invention contemplates methods of selecting patients for treatment (whether in a normal hospital setting or clinical trial) based on sputum levels. As shown in FIG. 10, separating out patients with greater than 2 cc sputum levels in a defined period (e.g. 4 hours) could have a significant impact on mortality. Those patients having greater than 2 cc of sputum showed higher mortality. Therefore, selecting this group for aerosol treatment is warranted.

Figure 11:
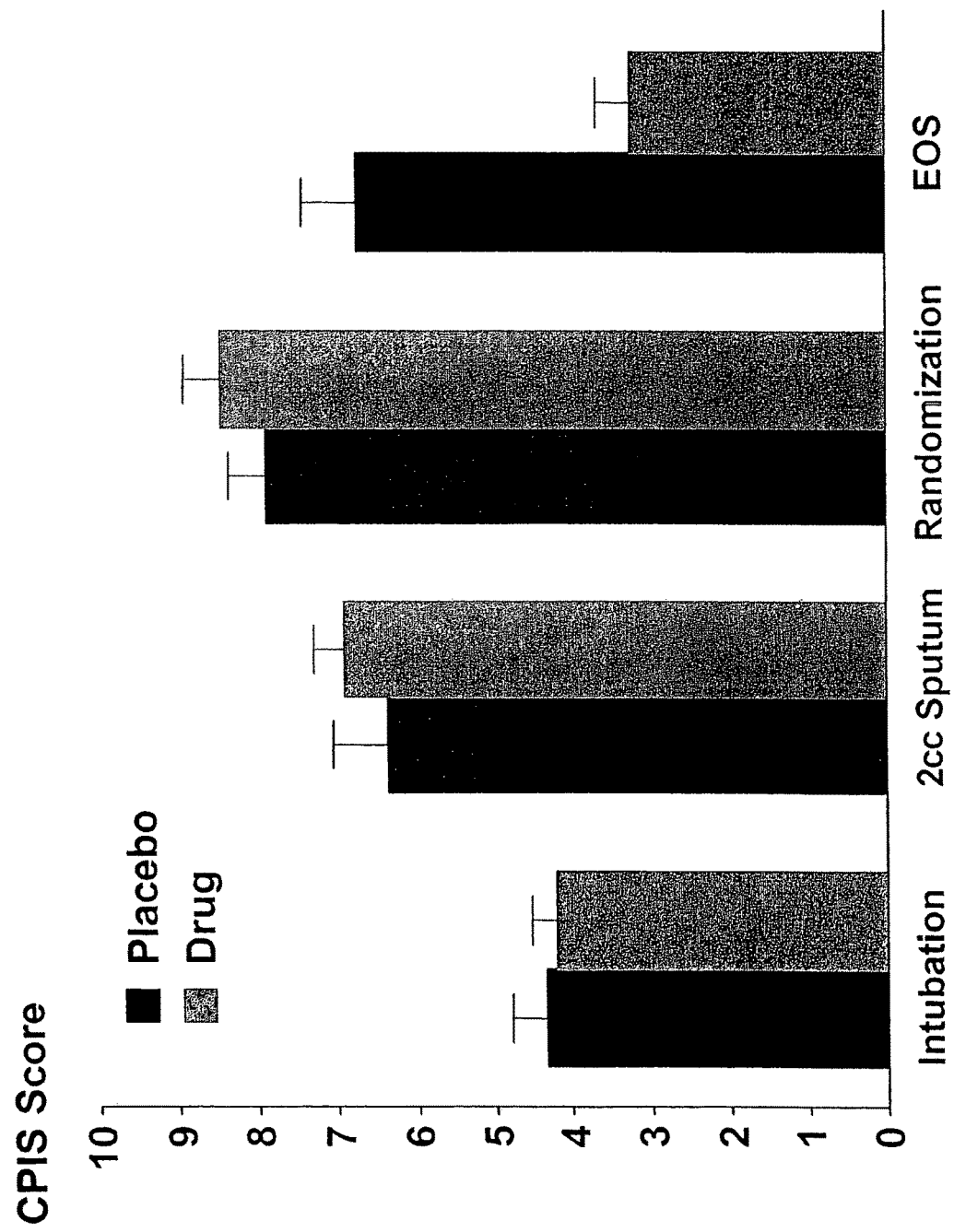
FIG. 11 is a bar graph showing the association of CPIS Score with sputum levels and post-treatment at the end of the study (EOS).

FIG. 11 shows how the CPIS score together with sputum levels might be used to select patients for treatment. At the time of intubation, patients exhibited a CPIS score of approximately 4. At the point where 2 cc of sputum was being secreted, the CPIS score was 6 or greater. At the time of treatment in the study (i.e. the point where the patients were randomized to receive drug or placebo), the CPIS score was even higher. However, at the end of treatment, the drug treated population showed a dramatically reduced CPIS number.

The data of FIGS. 10 and 11 suggest a treatment modality (whether in a normal hospital setting or for clinical trials to evaluate devices and drugs) wherein intubated patients with a sputum level of 2 cc or greater are scored using the CPIS system. Those having less than a CPIS score of 6 are not treated systemically with antibiotics. Rather, they are treated with aerosolized drug (e.g. antibiotic cocktail, etc.). Of course, for a clinical trial, one group is randomized for drug and the other placebo. In any event, all patients are given a daily CPIS score. The CPIS score for the treated group should decline (along with sputum levels). The end points contemplated include, but are not limited to, days on ventilation, development of VAP (as determined using the CDC-NNIS criteria), CPIS score, sputum levels, BALF cultures, and mortality—or combinations thereof (e.g. a CPIS score of 4 or less and less than 2 cc sputum secreted in 4 hours).

Those having a CPIS score of 6 or greater are first tested for direct evidence of infection (e.g. BALF with organisms as measured, for example by gram staining). Those patients who are negative (e.g. no detection by gram staining) are not treated systemically with antibiotics. Rather, they are treated with aerosolized drug (e.g. antibiotic cocktail, etc.). Of course, for a clinical trial, one group is randomized for drug and the other placebo. In any event, all patients are given a daily CPIS score. The CPIS score for the treated group should decline (along with sputum levels). The end points contemplated include, but are not limited to, days on ventilation, development of VAP (as determined using the CDC-NNIS criteria), CPIS score, sputum levels, and mortality—or combinations thereof (e.g. a CPIS score of 4 or less and less than 2 cc sputum secreted in 4 hours). Any rise in the CPIS score (and/or other marker of progressed disease, for example, patients with CFUs of 10,000 or more) results in systemic antibiotic treatment:

Those having a CPIS score of 6 or greater who are positive for organisms (e.g. positive by gram staining) are treated systemically with antibiotics. Thereafter (or simultaneously), they are treated with aerosolized drug (e.g. antibiotic cocktail, etc.). Of course, for a clinical trial, one group is randomized for drug and the other placebo. In any event, all patients are given a daily CPIS score. The CPIS score for the treated group should decline (along with sputum levels). The end points contemplated include, but are not limited to, days on ventilation, development of VAP (as determined using the CDC-NNIS criteria), CPIS score, sputum levels, and mortality—or combinations thereof (e.g. a CPIS score of 4 or less and less than 2 cc sputum secreted in 4 hours). Any rise in the CPIS score (and/or other marker of progressed disease, for example, patients with CFUs of 10,000 or more) results in continued systemic antibiotic treatment. Any decline in the CPIS score (or even just a stable CPIS score with CFUs of less than 10,000) results in discontinued systemic antibiotic treatment.

Formulation. The infections of the trachea and lung can be of different types. Some infections are viral; some are fungal (including yeast). More commonly, the infections are bacterial in nature. However, many cases of infection are not single organism infections; polymicrobial infections are documented. Combes A. et al., "Incidence and outcome of polymicrobial ventilator-associated pneumonia" *Chest* 121-1618 (2002). For this reason, in one embodiment, the present invention contemplates an antimicrobial mixture or "cocktail."

In one embodiment, the mixture comprises two or more antimicrobials (e.g. antibiotics) formulated for aerosolization. In a preferred embodiment, the antibiotic combination is selected for the ability to combat a wide spectrum of gram-positive and gram-negative organisms. In this embodiment, testing may be done prior to treatment to confirm a combination of gram-negative and gram-positive bacterial growth in the airways. On the other hand, it is also contemplated that treatment with the preferred mixture can be done without testing or confirmation of the existence of both gram-negative and gram positive organisms. In the latter case, the exigencies of the ICU may make treatment with the mixture prudent as a precaution. Such an approach is justified in that the aerosolized mixture is directed locally to the infection with minimal (if any) systemic exposure. Treating with the preferred mixture may ensure against the possibility that the progression of infection into the distal airways is actually facilitated when one antibiotic regimen follows another. On the other hand, when the type of infection is known (or suspected due to indicators), treatment with a single antibiotic appropriate for the infection is contemplated.

In one embodiment, antifungals and antibiotics are used in a mixture. In yet another embodiment of the present invention, antivirals, antifungals and antibiotics are used in a mixture. In one embodiment, these mixtures are in particles (e.g. encapsulated particles, microparticles, etc.).

The present invention contemplates compatible antibiotic combinations that can be administered simultaneously in a common vehicle (or alternatively in separate vehicles that can be administered together or in series, such as within minutes to within 8 hours of each other) and can be expected to have similar (although not identical) therapeutic timecourses. The present invention contemplates providing such preparations in a formulation that is well-adapted for use in suitable aerosolization devices, since aerosol administration is an efficient means for administering the combination treatment directly to the surfaces of the affected airways while minimizing the exposure of other parts of the body to antimicrobial levels of antibiotic agents. Suitable aerosol delivery devices are those that deliver predictable amounts of therapeutic agents directly to the affected areas without picking up oropharyngeal bacteria and transporting them to the deep lung on the one hand, and without disturbing the normal oropharyngeal flora by antibiotic attack on the other. Suitable aerosol delivery devices are also those selected on the basis of the fact that, in operation, they do not develop blockages due to thicker (and/or more adhesive) formulations.

In another aspect, the present invention provides a pharmaceutical composition comprising, in combination, an anti-gram-positive antimicrobial agent and an anti-gram-negative antimicrobial agent and a pharmaceutically acceptable carrier, excipient and/or diluent selected for compatibility with the antimicrobial agents and capable of being aerosolized. It is not intended that the present invention be limited to particular carriers, excipients and/or diluents. A variety of such agents are contemplated. In some embodiments, formulations will include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions or dry powders, and typically contain 1%-95% of active ingredient, preferably 2%-70%.

While the present disclosure places an emphasis on human treatment, the therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

Detailed Description of The Invention

The certain preferred embodiments of the present invention, delivery of the aerosol is done in a manner that avoids the variability of humidity and other factors (e.g. flow rates, differences in tubing, differences in the ventilator, etc.). In one embodiment, this involves the use of an aerosol generator (whether via a nebulizer, an aerosolizing catheter, or the like) positioned between the patient and the junction (typically a Y piece) of the inspiratory and expiratory lines. In some embodiments, the aerosol generator is attached to (or an integral part of) the Y piece. The advantages of certain embodiments are discussed below in relationship to conventional arrangements.

Figure 9A:
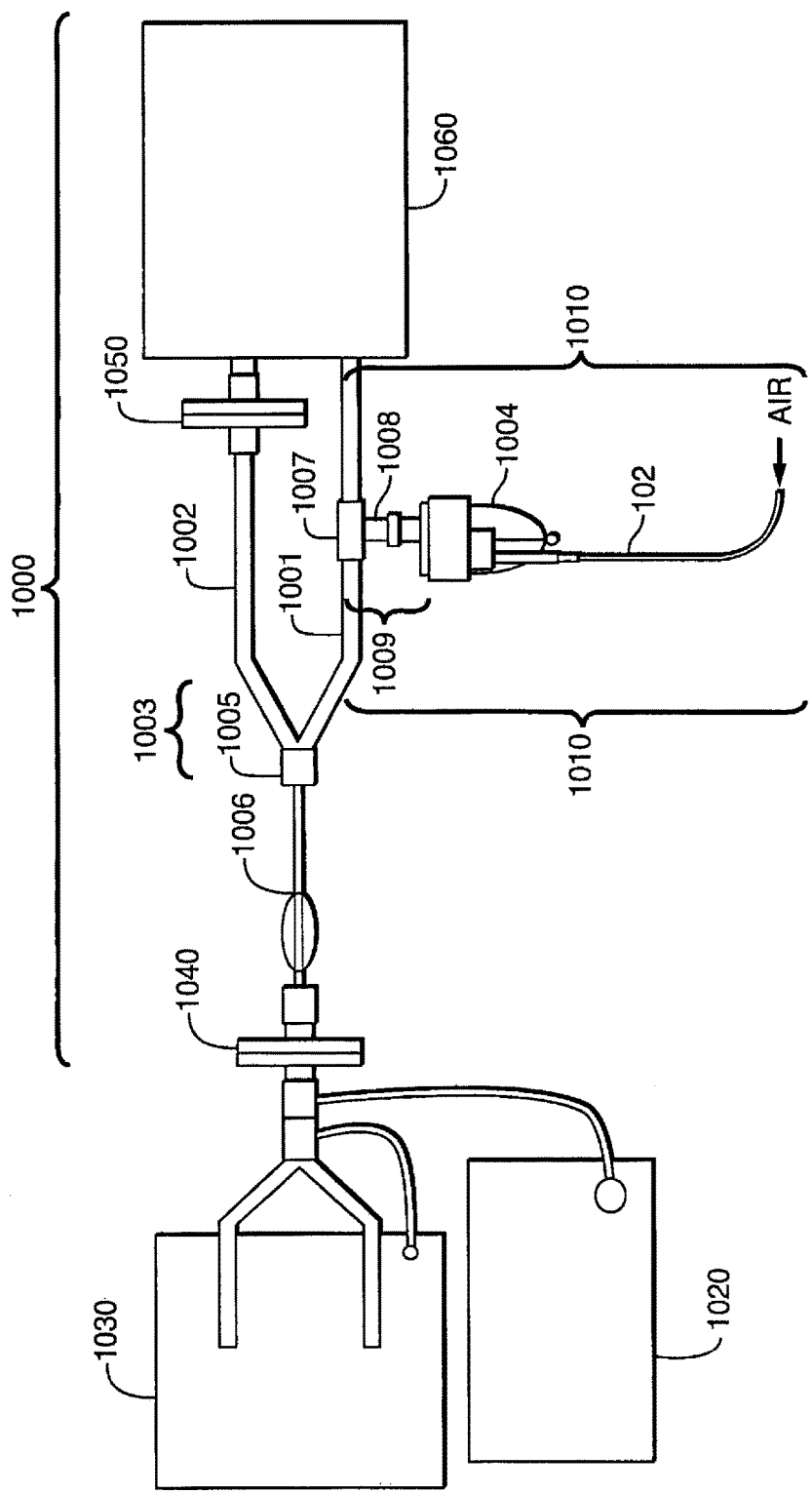
FIG. 9A is one embodiment of a bench model for testing aerosol delivery as a function of ventilator conditions (e.g. humidity, breathing cycle, etc.).

Humidity-sensitive nebulization. For any given ventilator and nebulization device, a suitable predetermination of the humidity to be selected may be made using a bench model (FIG. 9A). In use, a test ventilator is connected to a test lung (e.g., M.I.I. VentAiTTL, Michigan Instruments, Inc., Grand Rapids, Mich.) via a number 8 endotracheal tube. Aerosols are sampled just distal to the endotracheal tube with an inhaled mass filter, (Pari, GmbH, Starnberg, Germany) and a leak filter in the expiratory line. Aerosols are generated by nebulization with the device located in the inspiratory line 12 inches from the Y piece. Any of a number of test substances may be employed. Among the variables that can be evaluated for each ventilator are:

Relative humidity in the ventilator circuit
Frequency and timing of nebulization events during the ventilator cycle (the "nebulization algorithm")
Bias flow rate
Elements of nebulizer performance (drive pressure, initial particle size, powder aerosol, liquid aerosol, anti-hygroscopic enrobement aerosol formulations, etc.)
Parameters measured for each of the variables are:
Inhaled Mass (%), the amount of drug on the filter as a percent of the nebulizer charge
Mass Balance (% Recovery), the sum of both filters plus remnant activity in the nebulizer
Mass Media Aerodynamic Diameter (MMAD)

The artisan will find in the bench test of any given ventilator a humidity setting that maintains the MMAD of the aerosol within the preferred range of the invention as a function of bias flow rate, the nebulization algorithm and the specific performance of the nebulizer. In the case of the arrangement shown in FIG. 9A, good delivery of aerosolized drug can be achieved by actuating the nebulizer when the humidity feature of the vent is not active. Thus, in one embodiment, the present invention contemplates the delivery of a formulation comprising two or more antibiotics using an arrangement wherein the nebulizer is positioned in the inspiratory line. Preferably, this embodiment is employed under modified humidity conditions (i.e. conditions such that humidity does not significantly impair delivery).

Figure 9B:
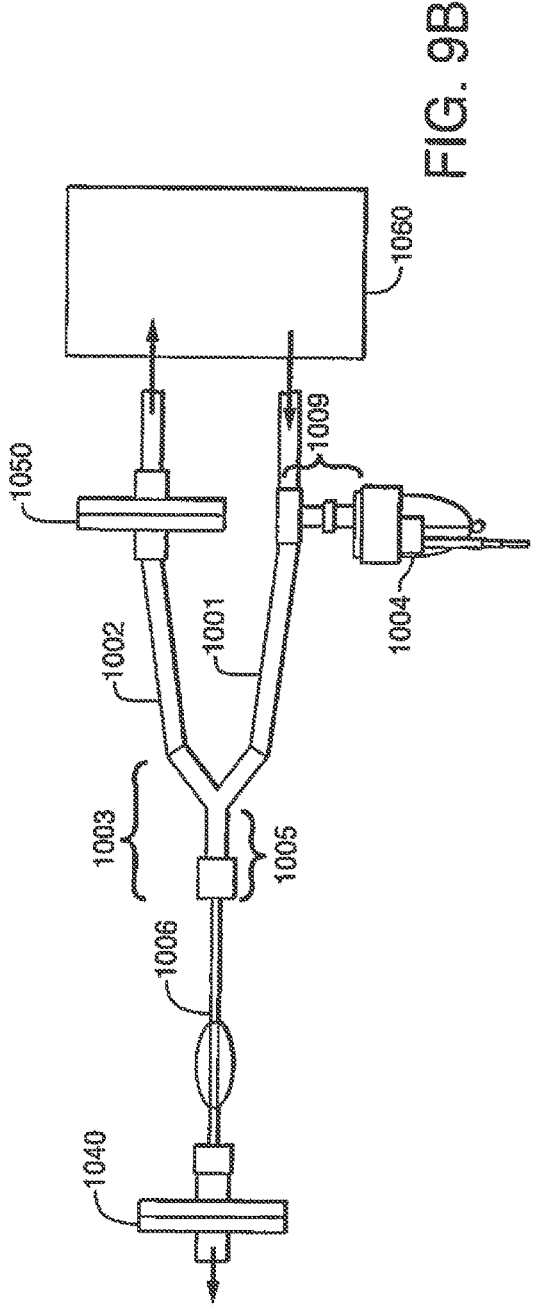
FIG. 9B is another embodiment of a bench model for testing aerosol delivery, wherein the aerosol source is not linked to the inspiratory line of the vent.
Figure 9B:
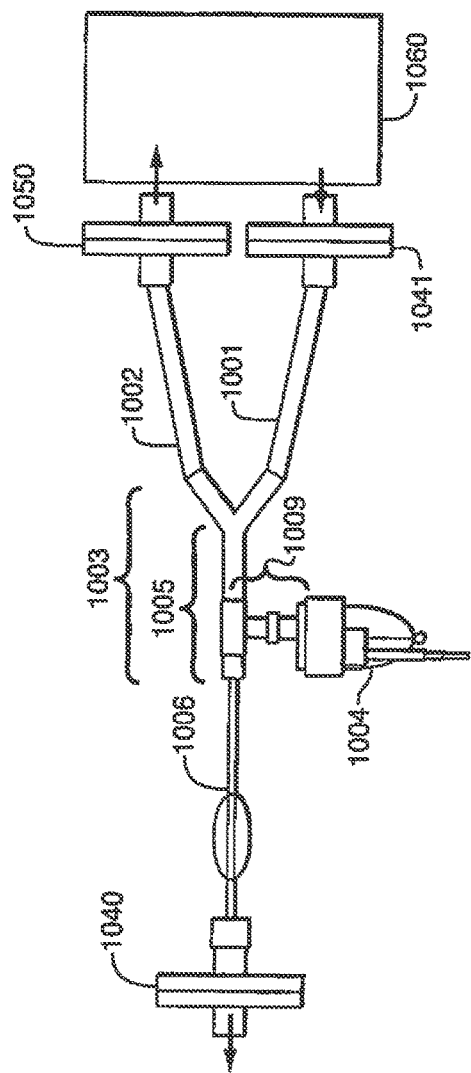

Another embodiment of a bench model is shown in FIG. 9B. Again, aerosols are sampled just distal to the endotracheal tube with an inhaled mass filter, (Pari, GmbH, Starnberg, Germany); optionally, Expiratory and Inspiratory line filters can be employed. Aerosols are generated by nebulization with the device located outside of the inspiratory line (i.e. not in the inspiratory line) and within the Y piece (preferably toward the end of the Y piece that connects with the ET tube). Again, any of a number of test substances may be employed. Of course, the present invention contemplates, in one embodiment, using the arrangement of FIG. 9B in the context of a patient, wherein a formulation comprising at least one antibiotic is aerosolized and administered. With the embodiment represented in FIG. 9B, a more consistent (albeit lower efficiency) dosing is observed. This illustrates one advantage of aerosol entry in the Y piece.

Non-hygroscopic enrobement of aerosolized therapeutic agent. A large number of microencapsulation technologies are known in the art, many of which will render the aerosolized particles of the invention resistant to rainout onto the walls of the humid ventilator circuit. Although any aerosol particle that is anhygroscopic is with the scope of the invention, a recently disclosed and particularly apt technology for the enrobement purpose is described and claimed in U.S. Pat. No. 6,403,057 to Schneider and Bussat, and is incorporated herein by reference. According to that invention, a microcapsule with a mean size from a fraction of a μm to 1,000 μm may be obtained when one or more biodegradable, water insoluble lipids are used to encapsulate a core which comprises, initially, air or a gas. The process results in microcapsules of significant mechanical strength in the form of a non-coalescent, dry and instantly dispersable powder. Composed as they are of biodegradable lipids, the microcapsules last in the body for one to a few hours.

Although the microcapsules retain a core of gas, they can be used for the delivery of therapeutically active substances, in which case the active substance may be included in the membrane or may be loaded in the core. Virtually any biologically active substance can be used with the microcapsules.

To administer the microcapsules in the context of the instant invention, the artisan "loads" the capsules according to the teaching of the '057 patent and uses the resultant particles in the same manner as any other dry powder, giving due attention to the "charge" of active agent within the microcapsules, the "charge" of the nebulizer and its performance properties, and the settings of the ventilator.

Dose-control device. The calibration test described above permits the artisan to predetermine with precision the amount of antibiotic that should be used to "charge" the aerosolization devices utilized in the invention. Such charge, furthermore, is a far lesser amount than the prior art teaches (i.e., the amount that would be administered systemically). While syringe-like delivery can be used in the context of the present invention with hand-actuated pressure, such approaches run the risk of operator error and mis-dosing. Accordingly, in a preferred embodiment, the invention provides a device comprising a pre-measured drug reservoir sized to contain only that amount of drug desired, wherein delivery—once triggered—is automatic and complete. By making delivery automatic, the present invention contemplates that, when administered by the methods of the invention, the administered dose will elevate sputum levels of the antibiotic above MIC without elevating systemic levels significantly. Ideally, antibiotic levels are elevated in the extracellular fluid on the mucosal surface of the area of the lung and/or trachea that is infected.

Figure 8:
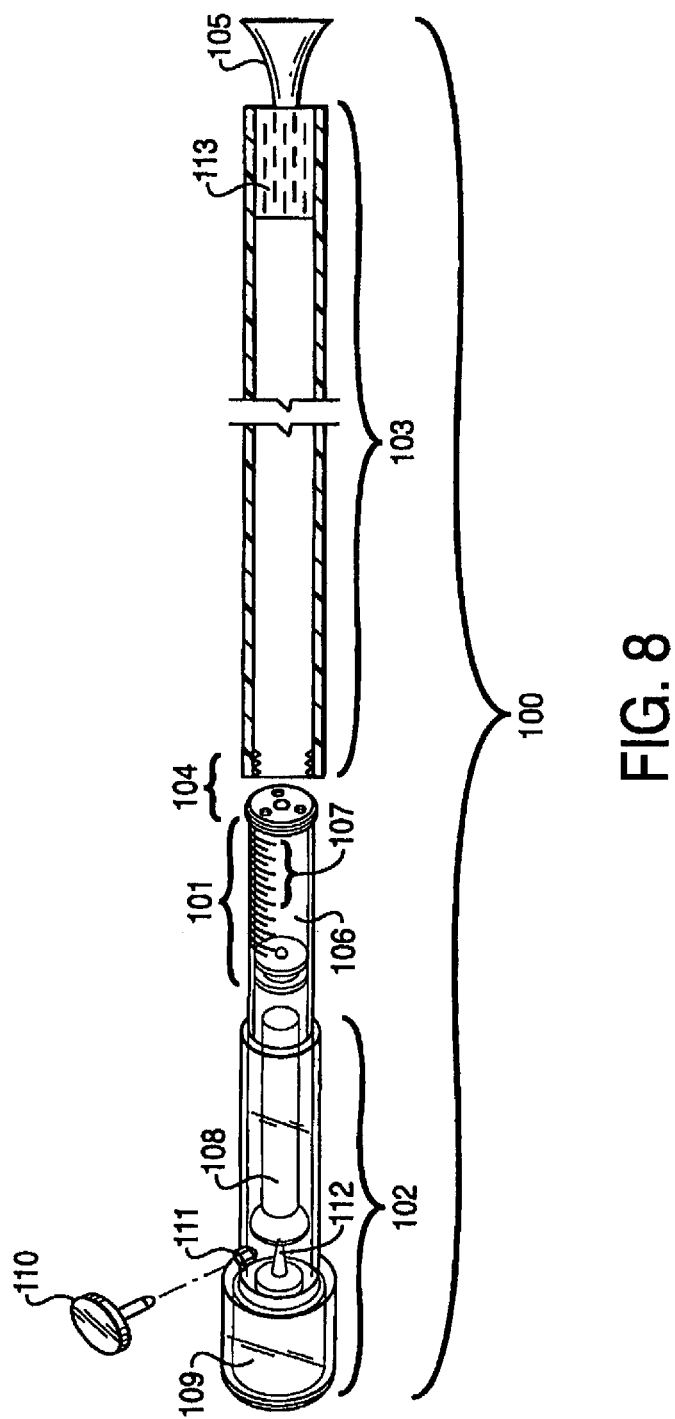
FIG. 8 is a diagram of a preferred device of the present invention comprising a dose metering element, a fluid driving element, and an aerosolizing catheter. The particular embodiment shown depicts a first portion of the device (comprising the dose metering element and fluid driving element) as modular and configured, to engage the second portion of the device (e.g. in a screw/thread engagement) comprising the aerosolizing catheter, the catheter comprising an external baffle.

FIG. 8 shows one embodiment of a stand alone device which provides dose-control. In the embodiment shown, the device (100) comprises a dose metering element (101), a fluid driving element (102), and an aerosolizing catheter (103). While it is not intended that the particular embodiment shown be limiting in any manner, for convenience the device can be fashioned in two portions. The particular embodiment shown depicts a first portion of the device (comprising the dose metering element and fluid driving element) as modular (to permit—if desired—single use, disconnection, and disposal of the first portion, followed by a second administration of the formulation with another modular unit) and configured to engage the second portion of the device (e.g. in a screw and thread engagement, 104) comprising the aerosolizing catheter, the catheter comprising an external baffle (105)

In a preferred embodiment, the dose metering element comprises a reservoir of defined volume, said reservoir (106) being preferably configured as a transparent or semi-transparent cylinder or tube, with or without visible measurement indicia (107). In this preferred embodiment, the fluid formulation (e.g. antibiotic formulation) for the patient is placed in the reservoir, the reservoir (106) being downstream (in terms of the direction of flow) of the fluid driving element (102). In a preferred embodiment, the fluid driving element comprises a plunger or piston (108) driven by compressed gas (not shown), said compressed gas stored in a container or canister (109) and released by the operator of the device (not shown) via a trigger (110) which engages the device through a port (111), allowing the trigger (110) to break a restraint/release (112). When the release of compressed gas is triggered, the plunger or piston (108) pushes the defined volume of the formulation into the aerosolizing catheter. In a particularly preferred embodiment, the device is a "stand alone" device configured such that it can engage an opening or port in a ventilation system (e.g. see FIG. 1B), wherein said aerosolizing catheter (103) (having an aerosolizing nozzle, 113, at the delivery end) is of such dimensions such that it can to fit inside (e.g. see FIG. 6)—or alongside—an endotracheal tube (and/or tracheostomy tube) of an intubated patient, such that the delivery end (i.e. out of which the aerosol is delivered) of the catheter extends approximately to the end of the tube (or preferably below the end of the tube, thereby delivering aerosol in a manner that bypasses the tube). In a particularly preferred embodiment, the end of the aerosolizing catheter comprises a baffle (105) to slow the speed of the aerosol.

It is not intended that the present invention be limited by the precise design of the driving element, triggering elements, catheter and baffle shown in FIG. 8. Variations on these elements are contemplated, such as those shown and described in U.S. Pat. Nos. 5,642,730, 5,964,223 and 6,079,413 (all of which are hereby incorporated by reference and show various different designs for catheters, aerosolizing nozzles, baffles, etc) and U.S. Pat. No. 6,210,359 (hereby incorporated by reference).

In a preferred embodiment, the driving element can be avoided entirely by the use of an Aerogen™ aerosol generator. In such an embodiment, the reservoir is placed at the delivery end of the catheter, which terminates with the Aerogen™ aerosol generator. On the other hand, the present invention also contemplates substituting the aerosol nozzle in FIG. 8 with the Aerogen™ aerosol generator. Of course, the present invention is not confined to the current size of the commercially available Aerogen™ models. The aerosol generators may be downsized by conventional engineering in order to conveniently attach to other devices. For example, in one embodiment, the aerosol generator is as small as approximately 0.4 to 10 mm, with a preferred size of approximately 4.0 mm (which is a convenient size for an adult endotracheal tube).

Figure 12:
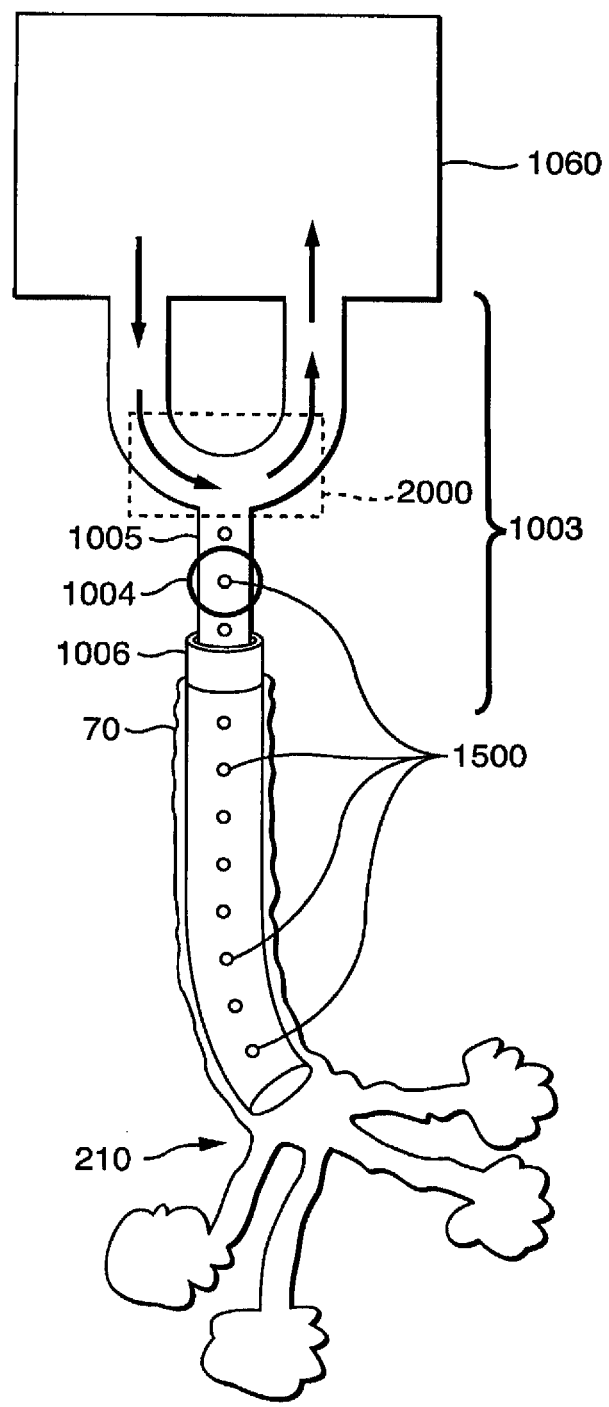
FIG. 12 is a schematic of one embodiment of a Y piece for use with a ventilator, showing numerous alternative placements of an aerosol generator in the lower part (e.g. distal arm) of the Y piece.

Alternatively, an aerosol generator (e.g. one of the Aerogen™ models or a scaled down version thereof) can be included in a constructed Y piece on a vent. FIG. 12 is a schematic of one embodiment of a Y piece for use with a ventilator, showing numerous alternative placements of an aerosol generator in the lower part (e.g. distal arm) of the Y piece. Indeed, the entire distal arm of the Y piece is contemplated as "aerosol capable." Importantly, it has been found that a more consistent dosing can be achieved where the aerosol generator is placed below the a region (the approximate bounds of this region are shown by dotted lines in FIG. 12).

In one embodiment, the aerosol generator is placed in the lower arm of the Y piece with a dosing catheter attached. In another embodiment, the aerosol generator is integral to the Y piece (e.g. attached, embedded therein, inserted, etc.) such that the delivery end (or tip) of the aerosol generator is able to deliver drug into the lumen of the tube. In one embodiment, the aerosol generator extends into the lumen of the tube. In one embodiment, the aerosol generator extends through the walls of the tube.

In one embodiment, the present invention contemplates that the Y piece with the integral aerosol generator (e.g. loaded with drug at the site) is modular and can be supplied as a "stand alone" device. In such an embodiment, to deliver drug (e.g. a cocktail of antibiotics) one removes the regular Y piece associated with commercial ventilators replacing it with the modular Y piece comprising the aerosol generator (e.g. in the manner of an "armed warhead"). Thereafter, drug delivery is achieved by actuating the generator.

It is not intended that the present invention be limited to a precise configuration of the modular tube (e.g. the upper portion of the Y tube might be shaped as a "V"; the Y tube might be shaped more as a "T"; etc.). Similarly, it is not intended that the present invention be limited to a precise placement position of the aerosol generator in the lower arm—or the number of aerosol generators placed therein (e.g. a plurality is contemplated in some embodiments; in one embodiment, the number of drug-loaded generators is determined by the desired dose of drug—i.e. the more drug desired, the more locally drug-loaded generators are used). Nor is it intended that the present invention be limited to placement of an entire aerosol generator inside the tube.

In one embodiment, the delivery end of the generator is integral to the lower arm of the Y piece, while other elements are attachable thereto. For example, in one embodiment, the drug delivery end of the generator is attached via a conduit (e.g. a pipe, tube, channel, etc.) to a drug supply (e.g. fluid reservoir) that is remote from the drug delivery end (e.g. aerosol head). Similarly, the force to deliver the drug may or may not be remote from the aerosol head. Local forces might be generated with a battery. Remote forces might be facilitated by a variety of appropriate energy transfer means (e.g. wire/electricity; conduit/fluid pressure and/or flow; mechanical transducers/sound).

Combination suction—and aerosol-catheter. In one embodiment of the method of practicing the invention, an aerosol-delivery catheter is utilized and is introduced through a port in the ventilator circuit (FIGS. 2A and 2B). It is convenient to utilize a suction catheter to serve as a guide for placing the aerosol catheter by providing a channel in the suction catheter such that the aerosol catheter can be threaded therethrough (see FIG. 6). In particular, the present invention contemplates an embodiment wherein a suction catheter is adapted (or adaptable) as a conduit for inserting an aerosolization catheter endotracheally. In a preferred embodiment, the suction catheter is part of the ventilator circuit, the ventilator circuit being equipped with an in-line (and in some embodiments, integral) sputum volume gauge.

In accordance with an embodiment of the present invention, a suction catheter, the tip of which in operation is situated distal to the endotracheally tube, is used for quantifying sputum volume in a ventilated patient and to serve as a conduit for placement of the aerosolization catheter. In a preferred embodiment, the suction catheter includes a suction tube indwelling in a pulmonary tree of a ventilated subject for suctioning sputum from the ventilated patient, a specimen trap for receiving and containing the sputum suctioned from the patient via the suctioning tube, and a closeable aerosolization catheter insertion port. The operative combination of trap and suction catheter provide a preassembled sterile unit that is not subject to contamination that separate units have. Preferably, the suction catheter is attached to the top of the trap with a sterile connection.

In accordance with other aspects of the invention, the suction catheter may include an EBC sensor (FIG. 2C) for measuring aerosolized components within the airway of the patient. A commercially available sensor which measures the inflammatory mediators may be used.

Referring to the drawings, the suction catheter 10 includes a port 14 which can be used either for attaching an aerosol catheter or an EBC collection circuit. FIG. 2B shows the suction catheter 10 with a proximal end of an aerosol catheter 30 inserted in the port 14. The distal end of the aerosol catheter 30 is attached to a liquid feed and a high pressure source. In a preferred embodiment, the aerosol catheter comprises multiple lumens. FIG. 2C shows the suction catheter 10 with a proximal end of an EBC collection circuit 32 inserted into the port 14. The distal end of the EBC collection circuit is connected to a vapor condenser.

By providing the port into the ventilator circuit (and in particular, a port positioned, in certain embodiments, at the end of the suction catheter nearest the patient), the present invention standardizes the placement of preferred delivery means such as the catheter variously described in U.S. Pat. Nos. 5,642,730, 6,079,413 and 6,293,279 (all of which are hereby incorporated by reference) so as to ensure delivery of the therapeutic agent directly into the relevant space (e.g. near the end of the endotracheal tube and, in preferred embodiments, just past the end of a properly positioned endotracheal tube) in a controlled and evenly dispersed fashion. Therefore, drugs for which dose is critical, such as antibiotics, can for the first time be administered to the lung safely and economically. Accordingly, such dose-critical drugs are now more likely to be approved by regulatory agencies for administration directly to the lungs. Moreover, for antibiotics specifically, the instant invention provides a reliable and objectively measurable delivery approach. When coupled with the above-discussed clinical indicator(s) for commencing treatment, the combined features offer optimum treatment results.

Preferred Drugs. Antibiotics useful in the invention as anti-gram-positive agents include the macrolides (e.g., erythromycin, clarithromycin, azithromycin) and the glycopeptides (e.g. vancomycin and teicoplanin). However, any anti-gram-positive agent capable of being dissolved or suspended in a suitable aerosol is within the scope of the invention (oxazoldinone, quinupristin/dalfopristen, etc.). Antibiotics useful as anti-gram-negative agents include aminoglycosides (e.g., gentamicin, tobramycin, amikacin, streptomycin, netilmicin); quinolones (e.g., ciprofloxacin, ofloxacin, levofloxacin); tetracyclines (e.g., oxytetracycline, doxycycline, minocycline) and cotrimoxazole. However, any anti-gram-negative agent capable of being dissolved or suspended in a suitable aerosol is within the scope of the invention (e.g. colistin, imepinim, meripenim, etc.). Preferably, the anti-gram-positive antibiotic and anti-gram-negative antibiotic are selected to have therapeutic time-courses not so disparate as to result, de facto, in treating the infection serially.

The fluid that serves as aerosolization vehicle is typically a buffered saline solution with a pKa selected to optimize the solubility and stability of both of the antibiotics selected for a particular formulation. Other fluids, however, including lipophilic vehicles including liposomes, are within the scope of the invention. For example, lipid or liposome formulated antibiotics resulting in sustained or controlled release of medication (e.g. Transave, SLT™ technology Inc., ALZA's Stealth Liposomal Technology, Gilead Lipsomes Drug Delivery systems). The concentration of each antibiotic selected for use in the invention is determined for a given aerosolization fluid by first selecting a rate of aerosol delivery. Then a sufficient amount of each antibiotic is added to deliver an amount to the airway of the animal that will increase the level of antibiotic in the systemic circulation by not more than the level conventionally achieved (as measured by assays well-known in the art) when such antibiotic is administered systemically for the treatment of pulmonary infections. Preferably, the amount is sufficient to increase systemic levels by not more than about the level generally regarded as sufficient to exert an antimicrobial effect systemically. More preferably, the amount is less than an amount sufficient to increase systematic levels enough to exert any toxicity systemically or to affect flora in the body elsewhere than in the areas of the lung that are infected or are at risk of becoming infected.

In one embodiment, the present invention contemplates administering surfactant (or, more generally, "wetting agents") via aerosol—not for the intrinsic therapeutic effect of the surfactant, but as a delivery vehicle for drugs such as antibiotics. While not intending to limit the invention to any particular mechanism, it is believed that the properties of the surfactant operate to facilitate distribution of the antibiotic over the entire surface of the lung.

Reduced Resistance. While the successful use of the compositions, devices and methods of the present invention is not limited to any particular mechanisms (or the understanding of particular mechanisms), it is believed that the incidence of antibiotic resistance will decline if the high selection pressure of systemic antibiotic therapy is not present. Nonetheless, the compositions, devices and methods of the present invention can be used successfully even against a background of systemic antibiotic therapy. Aerosolized antibiotics prevent the development of resistance in the presence of systemic antibiotics.

In one study, of 9 patients receiving aerosolized antibiotics, 3 developed newly resistance organism while on systemic therapy. On the other hand, among the 8 control patients on placebo, 5 patients out of eight on systemic therapy developed a newly resistance organism. This data suggests that i) aerosol administration reduces the incidence of resistance; and ii) decreased resistance is not simply a benefit of the aerosol approach, it is an intrinsic property of the aerosol approach.

Drug-Impregnated Tubes. One aspect of the present invention contemplates an endotracheal tube or tracheostomy tube impregnated with one or more antimicrobials. In a preferred embodiment, a mixture of at least one gram-positive and one gram-negative antibiotic is used. In one embodiment, the antibiotic mixture may be applied as a surface coating of the endotracheal tube. In another embodiment, the antibiotic mixture may be incorporated into the endotracheal tube matrix during manufacturing. In one embodiment, the antibiotic mixture is applied to the entire endotracheal tube. In another embodiment, the antibiotic mixture is applied to the cuff and/or tip of the endotracheal tube.

Polymer surface coatings are known to provide long-duration release of antibiotics and other drugs from polymer surface coatings. This technology requires post-manufacture application of a polymer/antibiotic mixture to the surface of the endotracheal tube. Shikani et al., U.S. Pat. No. 5,762,638; and Domb et al., U.S. Pat. No. 5,512,055 (both herein incorporated by reference). Polymer coatings contemplated by the present invention may be applied to the exterior surface of the endotracheal tube. In certain embodiments, the polymers comprising these coatings may exhibit, but are not limited to, the following characteristics: i) the polymers are soluble or dispersible in solution in order to be disposed onto the outer surface of the endotracheal tube; ii) the polymers do not chemically react with any of the contemplated antibiotics; iii) the polymers are compatible with all of the contemplated antibiotics and form a uniform, solid, complex; iv) the polymers are capable of forming a uniform coating on the surface of the tracheal tube; v) the polymers are capable of forming polymer-antibiotic complexes which remain stable during storage, use and disposal thereof without significant loss of antibiotic. It is preferred that the contemplated polymers are both biocompatible and nonbioerodible. Both these characteristics ensure that the polymers will not react with body tissues nor be inadvertently released into the patient's body, respectively. The polymers contemplated by the present invention include, but are not limited to, polyurethane, polyurea, ethylene vinyl acetate, polyvinylchloride, polyesters, nylon, polycarbonate, polyethylene, polymethyl methacrylate, cellulose esters (i.e., ethyl, methyl and propyl), polypropylene, polystyrene, polytereflouroethylene, poly(ethylenevinyl acetate), elastomeric organosilicon polymers, poly(hydroxy alkyl esters, copolymers and combinations thereof. Preferably, the coatings are between 0.01 and 1.0 mm thickness and, most preferably, between 0.1 and 0.22 mm thickness. The polymer coatings may be formed by solvent casting, melting, dipping, spraying, brush coating or any other suitable method.

Endotracheal tubes impregnated with mixtures of gram negative and gram positive antibiotics may be constructed during manufacture. The liquified polymer is loaded with a mixture of gram negative and gram positive antibiotics. To disperse the antibacterial mixture into the polymer, techniques such as mixing the antibiotics directly into the polymer or solvent evaporation techniques such as those disclosed in U.S. Pat. Nos. 4,310,509 and 4,643,181 are used, both hereby incorporated by reference. Solvent evaporated techniques typically involve forming an emulsion of the antibiotics in a solvent, and mixing the emulsion into the polymer so that the antibiotics are uniformly dispersed as a separate phase throughout the polymer mixture. The solvents used to form the emulsion may be a single type of solvent or a combination of solvents selected from water or water soluble solvents such as methanol, ethanol, ethyl acetate, tetrahydrofuran and the like. Mixing of the emulsion typically occurs at low mixing rates, about 300 rpm, and at ambient temperatures. The antimicrobial agent is preferably present in an amount of about 0.1% to about 25% by weight of adhesive, more preferably about 1% to about 5% by weight. When using hydrophilic adhesives, amounts less than 1% may be used. This mixture is extruded until properly mixed and molded into an endotracheal tube including the cuff and tip areas. The polymer is allowed to solidify and is then removed from the mold. The catheter is then wiped with an isopropyl alcohol (w/w 30/40/30) solution. Alternatively, the antibiotic containing liquified polymer is limited to the mold area consisting of the cuff and/or tip areas of the endotracheal tube, whereas the remainder of the endotracheal tube is molded without a mixture of antibiotics in the liquified polymer.

Importantly, the measurement of sputum levels in the patient is contemplated as a convenient way to measure the efficacy of embodiments of impregnated tubes. For example, it is contemplated that new endotracheal tubes with impregnated antimicrobials (e.g. coatings on the entire device, coatings on the tip and/or cuff area of the device, etc.) can be compared with one another, other tubes, or the same tube (albeit without impregnated drug) on the basis of sputum levels (or other measurements associated with infection described above). Sputum levels offer a convenient readout in that they can be readily measured as a function of time over the intubated period. It is expected that certain impregnated embodiments will prevent or at least delay the onset of increased secretions, and consequently the onset of tracheobronchitis and VAP. The present invention contemplates that the testing of such devices (including but not limited to the testing in clinical trials) can be enhanced by using the sputum level test (described above) with or without other indicators of disease.

The examples below are merely provided to illustrate certain embodiments in greater detail and are not intended to be limiting in any manner.

EXAMPLE 1

An aspect of the present invention may be regarded as a method for quantifying sputum volume in a ventilated patient. In one embodiment, the ventilated patient is suctioned until there are no further secretions. The ventilated patient is then suctioned for a predetermined time period. If there is a predetermined amount of sputum while the ventilated patient has been suctioned up to the predetermined time period, the sputum is cultured and analyzed. A therapy order is written based on the analyzed culture.

In accordance with other aspects of the invention, the ventilated patient is suctioned early in the morning (e.g, at 6:00 A.M.) until there are no further secretions. The ventilated patient is suctioned a second time later in the morning (e.g., at 8:00 A.M.) until there are no more secretions.

In accordance with still other aspects of the invention, the ventilated patient is suctioned hourly for four hours. In accordance with yet other aspects of the invention, the predetermined amount of sputum is about 2 cc.

In accordance with further aspects of the invention, the therapy order is an order for aerosolized antibiotics to be delivered directly to the lungs.

In accordance with a related aspect of the invention, delivery of the aerosolized antibiotics is effected via an aerosolization catheter introduced directly into the lungs via the suction catheter.

In a still further related aspect of the invention, aerosol delivery via the aerosolization catheter is actuated by means of a pump and pressure, which pump and pressure feed may be integral to a mechanical ventilator or, optionally, independent thereof.

In accordance with yet further aspects of the invention, an initial therapy order is written prior to analyzing the culture and the initial therapy order is modified after the culture is analyzed.

In accordance with still further aspects of the invention, inflammatory mediators in the sputum are, measured. The inflammatory mediators may include TNF-alpha, interleukin-1-beta, and soluble-ICAM. These levels are measured on sol levels of the sputum using commercially available ELISA kits. Rising levels of these cytokines imply worsening inflammation.

In accordance with yet other aspects of the invention, aerosolized components of exhaled breath condensate (EBC) are measured. The aerosolized components may include TNF-alpha, IL-1 beta, IL-8, $H_2O_2$ nitrates, and nitrites.

EXAMPLE 2

Embodiments of the present invention provide a system and method for defining risk for and prevention of ventilator associated pneumonia. The method comprises means for quantifying sputum volume in mechanically ventilated patients and interpreting the value obtained by using a reference database in which pneumonia risk data and sputum volumes are correlated. Alternatively, or in combination with sputum volume measurements, the method comprises means for measuring the flux of inflammatory cells or mediators of the inflammatory process in the sputum over time. The system in one embodiment comprises a suction catheter adapted for practice of the method and for administering the treatment via an aerosolization catheter. In exemplary embodiments, the system also enables measurements of volatile or aerosolized components of exhaled breath condensate (EBC) that are reflective of developing bacterial infection. Exemplary embodiments of the present invention provide a means for determining the total inflammatory burden of the airway.

Referring now to the drawings wherein the showings are for purposes of illustrating preferred embodiments of the present invention only, and not for purposes of limiting the same, FIG. 2A illustrates a suction catheter 10 with an integral sputum volume gauge 12 and an aerosolization insertion port 14 with closure means 16 formed in accordance with the present invention in use on a ventilated patient 20. As is well known, sputum comprises the material that is coughed up from the windpipe, bronchi, and lungs. A small amount of clear sputum is normally produced by the lungs each day. The amount of clear sputum increases in any minor respiratory infection. The sputum volume gauge 12 of the present invention allows for the measuring and analyzing the secretions in ventilated patients 20 in order to determine what treatment, if any, should be prescribed for the ventilated patient.

The volume of secretions in ventilator patients has been studied in pilot studies. These studies generated the fundamental data leading to the development of the device of the present invention and the concept of using volume assessment as a clinical endpoint. This early data was followed by an investigation that determined the amount of secretions of all newly intubated patients over the first two weeks of their respiratory failure. This investigation demonstrated that:

(1) secretions increased the second week of intubation; and (2) patients with pneumonia had a measurably significant increase in secretions compared to those patients who did not have pneumonia.

EXAMPLE 3

Experiments have shown a marked increase in secretions in those patients who had pneumonia compared to those patients without pneumonia. The amount of secretions increased during the second week in those patients without pneumonia. More specifically, the sputum volume for patients with pneumonia increased from approximately 6 ccs in the first week of ventilation to approximately 8 ccs in the second week. For patients not having pneumonia, the sputum volume increase from approximately 1 cc in the first week to approximately 2 ccs in the second week.

Data supporting the validity of sputum volume as a marker of inflammation was demonstrated in investigations examining the relationship between sputum volume and inflammatory cells and cytokines. Aerosolized antibiotics were administered to chronically ill stable patients requiring mechanical ventilation. Treatment caused a significant reduction in the volume of secretions (p=0.002). In addition there was a marked reduction in organisms in these patients. Further, volume of secretions was related to neutrophil concentration, r=0.502, p=0.008. Further IL-1β was also related to volume, r=0.589, p<0.006.

Neutrophils increase significantly with volume. These cells may be causative as inflammatory mediators released from them may augment mucous production.

EXAMPLE 4

To further assess the effect of treatment on airway inflammation, a method of assessing the total "inflammatory burden" to the airway was devised by calculating the flux of inflammatory cell or mediators over time. Volume measurement is performed for a specified period. Cell count and differential cell count of types of inflammatory cells are performed on the tracheal aspirate. Inflammatory cytokines are measured from the sol phase of the sputum. The airway burden is defined for each inflammatory parameter using the following equations:

Neutrophil airway burden=($TCC$) cell/gm tracheal aspirate(% neutrophils)(ml/6 hours)

and sICAM-1 burden=sICAM-1 ng/ml (ml/6 hours)

There are two components to the total amount of inflammatory mediators in the airway over time. One is their concentration and the second is the volume of secretions over time. The total amount of mediator over time is reflected in this measurement. Neutrophil cell burden decreased significantly by 7 fold (p<0.014) and sICAM-1 increased by 2.5 fold (p<0.034). This method gives a direct quantitative measurement of the total airway inflammation at any point in time, whether a patient is off treatment or is on treatment, thus allowing real time measurement of need for response to treatment rather than waiting for a more ultimate and dire outcome such as survival.

Establishing clinical endpoints remains a major challenge in studies designed to prevent or treat ventilator associated infections. The 4 hour collection is a potentially important means for evaluating airway pathophysiology and response to drug therapy. Increases in sputum volume noted by nursing staff by gross visual assessment often trigger work up or treatment for tracheobronchitis by critical care specialists. In order to eliminate the inaccuracies of subjective impressions of sputum volume which are dependent on frequency and method of suctioning we devised the quantitative volumetric assessment over a 4 hour time period We have previously documented a decrease in volume in patients after aerosolized antibiotic therapy.

In this study, the decrease in respiratory secretions was associated with a marked reduction in Gram-negative isolates with eradication of all organisms in six out of nine trials. Further more, Gram-stains in seven out of nine trials had no Gram-negative bacilli during treatment suggesting the bacterial population had not been reduced only in cultures test but had been markedly decreased in the airway. There were no significant side effects. Despite very high sputum levels, serum levels were low or non detectable except in the one patient with renal failure. In addition, the emergence of persistently resistant isolates seen in prior human and animal studies involving topical therapy to the lower respiratory tract was not observed. Only three of twenty isolates were resistant post treatment and none were detected two weeks post treatment. The reason for the lack of resistance is unknown. The patients were not all treated at the same time, nor for as long a time as in previous studies. Further, the total dose of the drug to the body is less than in selective decontamination and the effects on total body flora are probably reduced. Additionally, the drug is delivered "directly" to the target organ, leaving the mouth and gut unaffected.

In vitro studies have shown that gene expression of these proinflammatory cytokines, TNF-alpha and Il-1β, is markedly augmented by lipopolysaccharides from Gram-negative bacilli and they in turn induce synthesis of endothelial adhesion molecules and other chemotactic cytokines. These molecules appear to regulate the influx of inflammatory cells, their activation, and release of enzymes such as elastase. In vivo human data are limited primarily to cytokine levels from patients with septic shock, trauma and ARDS when BAL and sputum levels of TNF-alpha and Il-1β have been reported to be elevated. In these unstable syndromes it is difficult to distinguish a systemic inflammatory response from a pulmonary process mediated by cytokines derived from alveolar macrophages and other airway cells.

This was the first study to assess, the effect of a specific therapy on the relationship of these cytokines to airway inflammatory cells and volume of secretions. We measured effects of drug delivery on indices of airway inflammation including TNF-alpha, Il-1β, sICAM-1 and neutrophil elastase. Not only was the volume decreased with aerosolized antibiotics but the decrease correlated with IL-1β and with neutrophil concentration. It was found that the concentration of Il-β correlated well with numbers of macrophages/gm (r=0.744, p<0.002), neutrophils/gm (r=0.710, p<0.0004) and lymphocytes/gm (r=0.597, p=0.005). This is of interest as macrophages are the primary cell of origin for I 11-β and this cytokine may assist in increased recruitment of neutrophils.

Treatment was associated with an increase of sICAM-1. This may represent increased shedding of membrane bound ICAM-1 from the surface epithelium during antibiotic therapy when the reduction in Gram-negative isolates may have been associated with a down regulation of neutrophil flux. Conversely, levels of sICAM-1 correlated inversely with levels of human leukocyte elastase (r=0.606, p=0.008) suggesting decreased shedding of membrane bound sICAM-1 during neutrophil recruitment when airway inflammation and elastolytic activity were maximal.

In summary, these studies show that nebulized antibiotics can be effectively delivered to mechanically ventilated patients and that this treatment results in measurable changes in clinical and airway inflammatory indices. Selective therapy with aerosolized antibiotics as described in this invention, specifically targeted to patients with increasing inflammatory secretions might decrease the incidence of nosocomial pneumonia while preserving oral and gut flora with limited bacterial resistance.

EXAMPLE 5

The embodiments of the device of the present invention assess sputum volume, which is used as an endpoint to trigger treatment for respiratory infection prior to the development of radiographically discernible pneumonia. One embodiment of the device of the present invention 10 measures sputum volume in a suction tube 18 indwelling in the pulmonary tree of a ventilated subject. This device 10 determines which mechanically ventilated patients 20 would benefit from treatment of airway infection before it progresses to pneumonia. In addition to the suction catheter, the present invention includes a sterile specimen trap 12, which contains a maximum of 2 cc of sputum.

Figure 14:
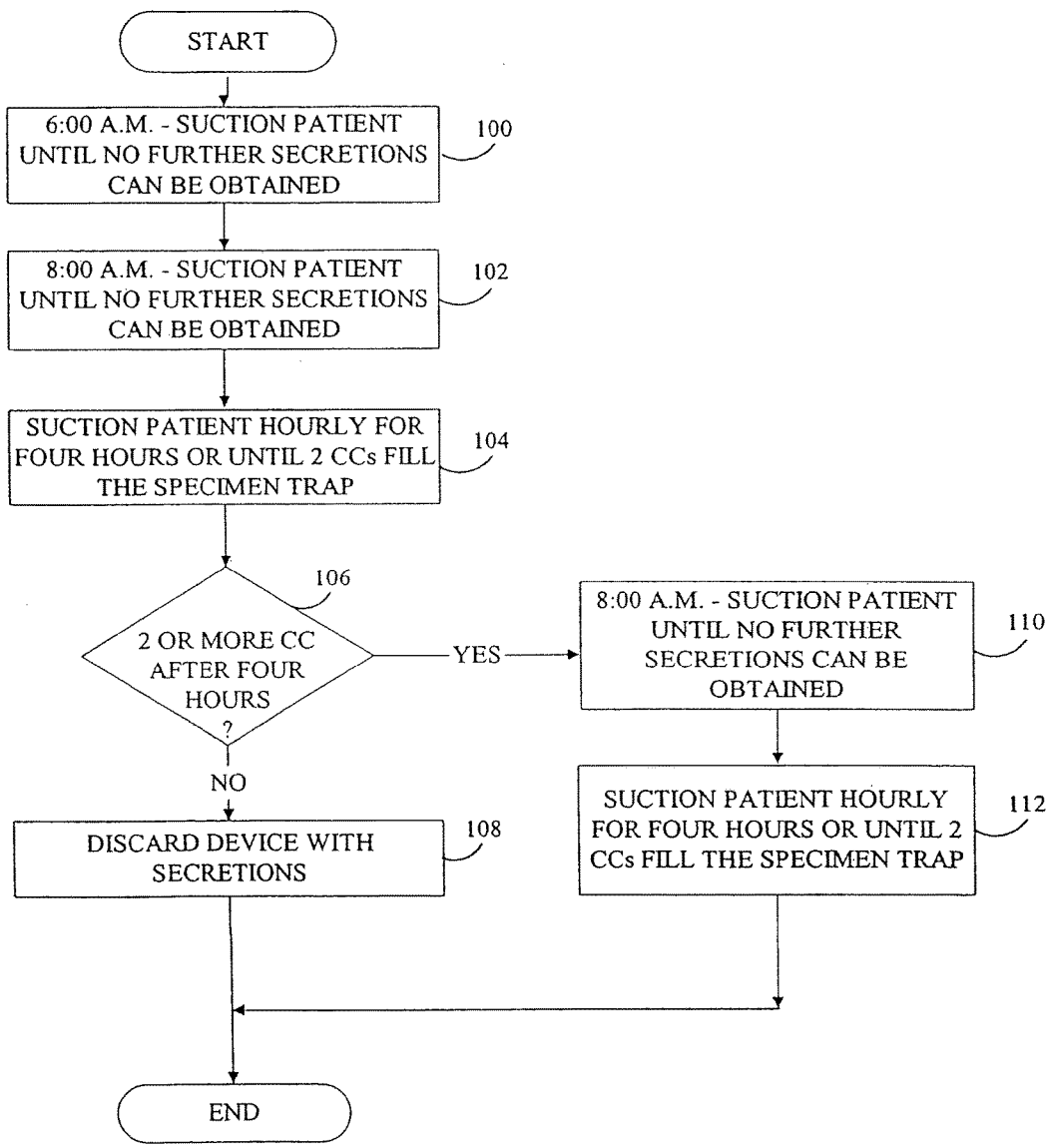
FIG. 14 is a flow diagram illustrating exemplary logic for measuring sputum volumne in a ventilated patient in accordance with one embodiment of the present invention

In exemplary embodiments, the present invention is used with the following protocol shown in FIG. 14. First, at 6:00 A.M., the patient is suctioned until no further secretions can be obtained (block 100). This ensures that the secretions that may have accumulated over night are not included in the timed quantitation period. No saline is used in the respiratory tract after this time. Any addition of saline will invalidate the volume of aspirate as this will no longer represent volume of airway secretions. Next, at 8:00 A.M., the patient is suctioned until free of secretion (block 102). The device 10 is placed in the suctioning circuit between the suctioning catheter and the negative pressure vacuum on the wall. The device 10 is made of plastic and must be sterile for use. While the device 10 requires no calibration, it does require a very specific protocol for suctioning which is part of its design.

The patient is suctioned hourly for four hours or until the sputum tap 12 is filled with 2 cc of secretions (block 104). If after four hours, there is less than 2 cc (no in decision block 106), the device 10 is taken out of the circuit line and discarded (block 108). If, however, there are at least 2 ccs (yes in decision block 106), the device is sent to Microbiology for culture and sensitivity analysis (block 110). An order is written to start the patient on aerosolized antibiotics at this point (block 112). Prior cultures or the predominant organism in the intensive care unit guides the antibiotic chosen. When the culture results are back (block 114), the order is modified (block 116).

Other embodiments of the present invention include a double endpoint diagnostic method comprising the contemporaneous measurement of suctioned sputum volume and the presence/level of inflammatory mediators in the sputum including, but not limited to, TNF-alpha, interleukin 1-beta, and soluble ICAM-1. The quantity of these mediators is dose related to sputum volume. Therefore, sputum volume and quantity of sampled mediators/molecules indicate developing infection.

Other embodiments of the present invention include a sputum volume/inflammatory mediator method that includes the measurement of volatile or aerosolized components of exhaled breath condensate (EBC) that are reflective of developing bacterial infection. EBC has been used to detect degrees of inflammation, but it has not been used to diagnose infection.

Various embodiments of the invention include a triple endpoint measurement wherein sputum volume, sputum mediators/molecules and condensate mediators/molecules together may be used to define the presence of bacterial infections. The suction catheter includes an EBC sensor as an integral part of its inline function. An EBC/volumetric device is placed in on the first day of mechanical ventilation and every day thereafter while this modality is required. Measurements of TNF-alpha, Il-1 beta and Il-8 (proinflammatory cytokines) in the secretions are monitored in addition to specific bacterial metabolic products in the breath condensate, e.g., $H_2O_2$, nitrates, nitrites and other nonspecified products. The integrated volume, secretion, and EBC inflammatory data quantifies the real-time changes on a daily basis providing information for therapeutic measure.

Exemplary embodiments of the present invention for treating and or preventing pneumonia by assessing the severity thereof according to a sputum volume test and devising an appropriate dosage regimen therefrom specify the use of Targeted Aerosolized Antibiotics (TAA) in those patients with increased secretions and inflammatory mediators/molecules. Patients who have increased volume and inflammation related to bacterial infections as determined by the volumetric/secretion/EBC device are begun on aerosolized antibiotics via the delivery catheter. This represents the concept of TAA.

Therapy is given for a defined period in only the targeted group. This lowers the antibiotic exposure to the patient and to the critical care unit environment. This is a fundamental aspect of this treatment as earlier studies using continuous topical therapy to all ventilator patients led to highly resistant organisms.

TAA leads to a fourfold improvement in patient outcome: (1) reduced incidence of ventilator associated pneumonia; (2) deceased days on mechanical ventilation; (3) decreased use of systemic antibiotics; and (4) decreased antibiotic resistance.

In order to confirm the reduction in the reduced incidence of pneumonia, an accurate and consistent means of diagnosing pneumonia is needed. The presence of fever, new infiltrate, leukocytosis, or leukopenia, purulent secretions and a quantitative bronchoalveolar lavage demonstrating greater than 10,000 colony forming units can be used. Using this methodology, endpoints can be compared which include:

(1) the incidence of pneumonia in those patients with increased volume and inflammation;

(2) the incidence of pneumonia in patients who receive aerosolized antibiotics versus placebo;

(3) the resistance patterns for treated patients versus the patterns in the intensive care unit environment;

(4) antibiotic use: number of antibiotics days/per patient=number of antibiotics per day times number of days in each critical care unit (e.g. 2 antibiotics per day times 7 days=14 antibiotic days); and (5) length on mechanical ventilation in treated and untreated patients.

EXAMPLE 6

Figure 15A:
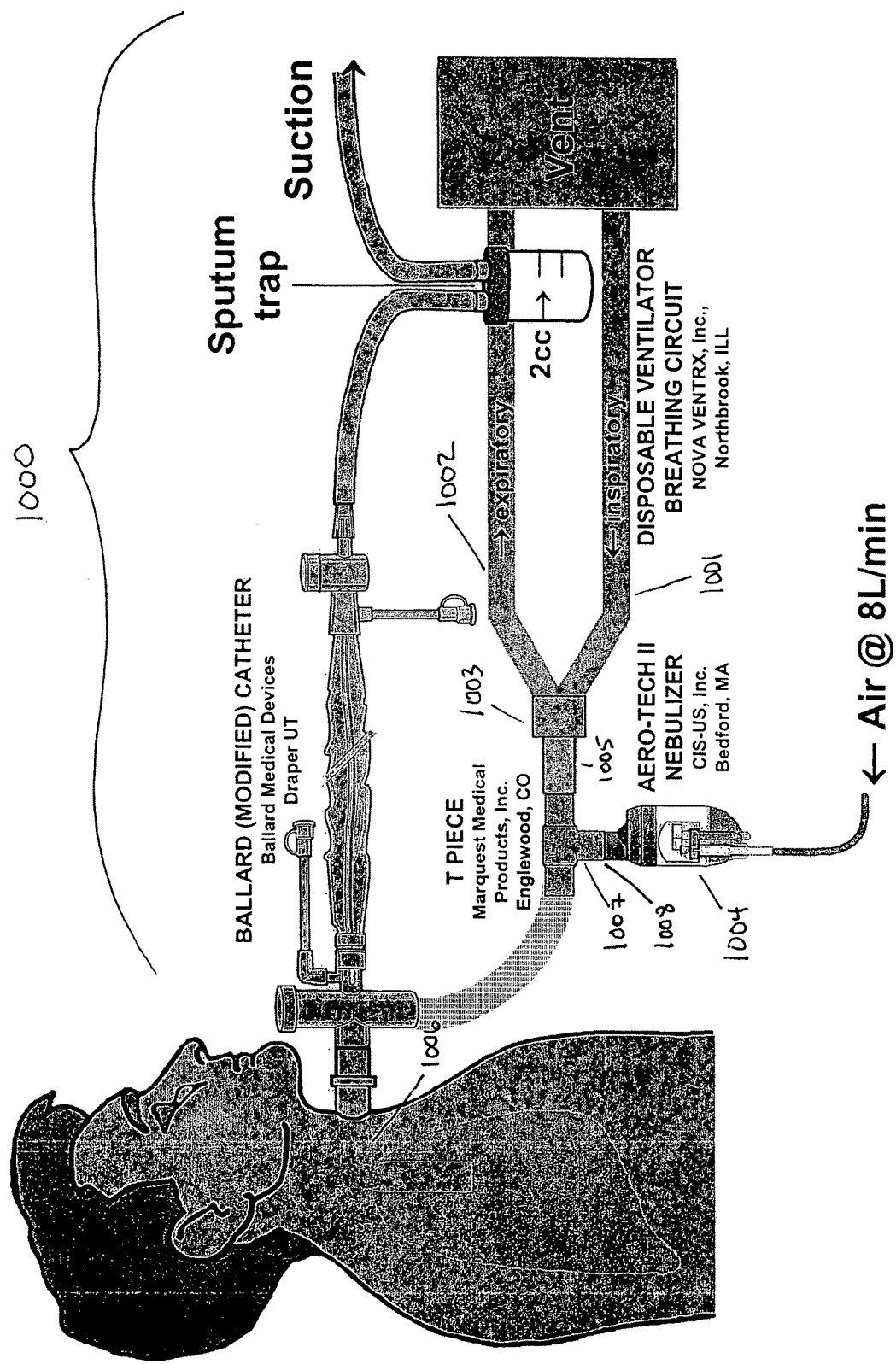
FIG. 15A shows one embodiment of a ventilator circuit comprising i) an inspiratory line and an expiratory line converging at a junction (typically a "T" or "Y" junction), ii) a nebulizer positioned in proximity to said junction (e.g. attached to the stem or integral to the stem) and in fluid communication with an endotracheal tube, wherein said nebulizer is not positioned in said inspiratory line or said expiratory line.

FIG. 15A shows a ventilator circuit (1000) comprising i) an inspiratory line (1001) and an expiratory line (1002) coming from a ventilator (shown as a box labeled "VENT") and converging at a junction (1003) (typically a "T" or "Y" junction), ii) a nebulizer (1004) positioned in proximity to said junction (e.g. attached to the stem (1005) or integral to the stem) and in fluid communication with a tracheostomy tube (1006) (or alternatively an endotracheal tube), wherein said nebulizer (1004) is not positioned in said inspiratory line or said expiratory line. While it is not intended that the present invention be limited to how the nebulizer is attached, FIG. 15A shows an embodiment wherein a Y-piece junction is attached to a commercially available T-piece (1007), wherein the Y-piece stem (1005) is connected to one arm of the T-piece (1007), and wherein the T-piece stem (1008) is connected to the nebulizer (1004).

Figure 15B:
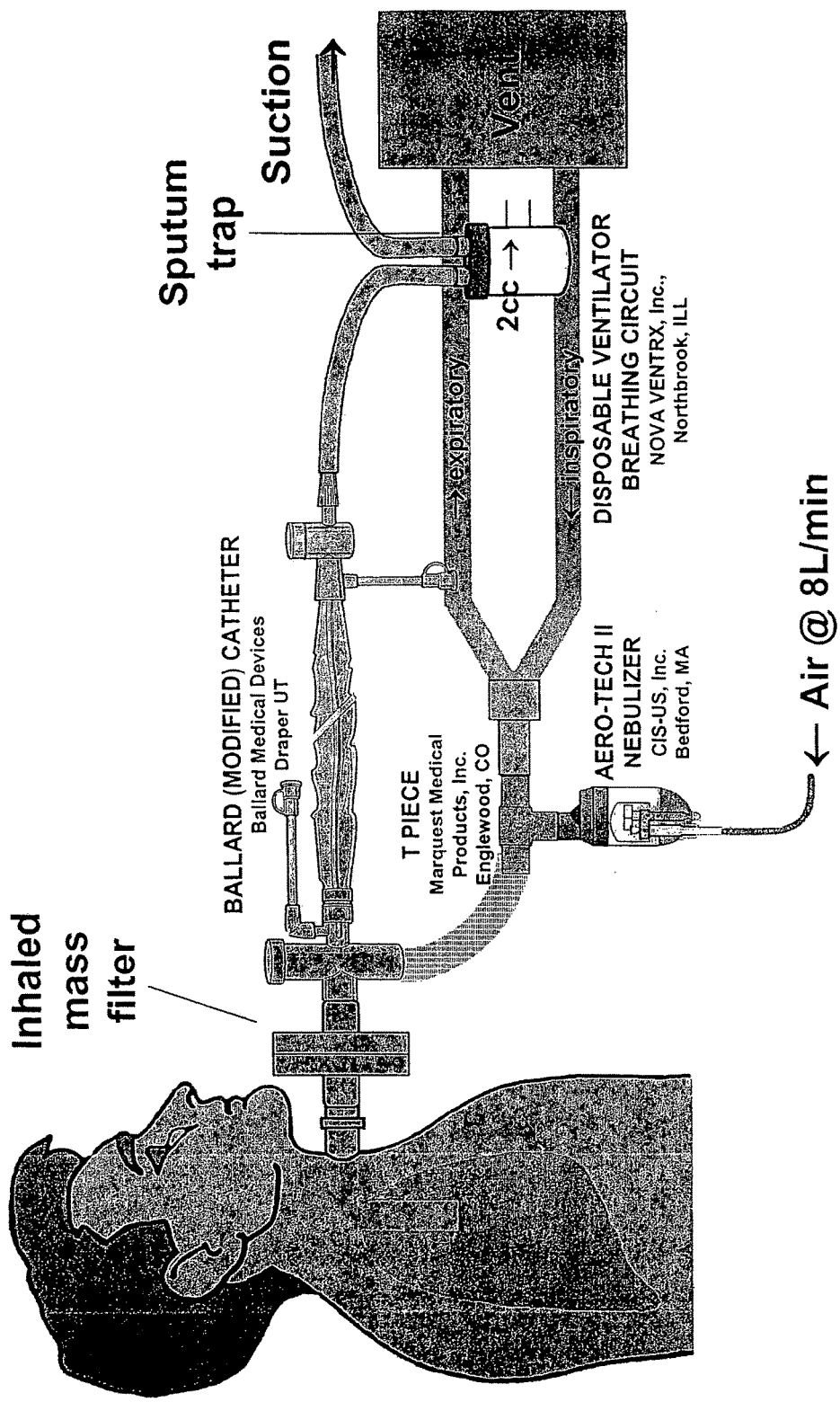
FIG. 15B shows a ventilator circuit comprising i) an inspiratory line and an expiratory line converging at a junction (typically a "T" or "Y" junction), ii) a nebulizer positioned in proximity to said junction (e.g. attached to the stem or integral to the stem) and in fluid communication with an endotracheal tube, and an inhaled mass filter removeably positioned (it can be introduced into the line to find out what the patient might be taking in—but must be removed before the patient can actually tak in any aerosol) between the nebulizer and the endotracheal tube, wherein said nebulizer is not positioned in said inspiratory line or said expiratory line. The inhaled mass filter allows one to do accurate measurements of what delivery amounts are actually reaching the patient.

FIG. 15B shows a ventilator circuit comprising i) an inspiratory line and an expiratory line converging at a junction (typically a "T" or "Y" junction), ii) a nebulizer positioned in proximity to said junction (e.g. attached to the stem or integral to the stem) and in fluid communication with an endotracheal tube, and a removeable inhaled mass filter positioned between the nebulizer and the endotracheal tube, wherein said nebulizer is not positioned in said inspiratory line or said expiratory line. The inhaled mass filter allows one to do accurate measurements of what delivery amounts are actually reaching the patient.

In a first experiment, the arrangements of FIGS. 15A and 15B were used with two different commercially available ventilators: the T-Bird ventilator, the Drager ventilator. The nebulizer actuation was examined in "continuous" mode as well as in a "breath actuated" mode. The humidity feature for these ventilators was examined by performing the test both when the feature is active and when it is off. An expiratory line filter was also used (not shown). Table 1 summarizes the data (as a percentage of nebulizer charge). Clearly, there is an advantage when delivering the aerosol (of albuterol) when the humidity feature is off and not active. When administration is breath actuated, the amount of drug on the expiratory filter drops by approximately 50% and there is some increase in inhaled mass when administration is breath actuated. Most importantly, the data reveal a narrow range (a range of approximately three percentage points) of inhaled mass (i.e. good control over the dose).

When compared with conventional arrangements for aerosolization, the data reveals that the placement of the nebulizer such that it is not in the inspiratory line improves control over the delivery dose. A more reproducible dose is delivered using the arrangement where the nebulizer is not in the inspiratory line (such as that shown in FIGS. 15A and B).

Importantly, while FIGS. 15A and 15B show the placement of the nebulizer at a particular position, the present invention contemplates embodiments wherein the nebulizer is not directly attached to the Y piece, but is placed closer to the patient (indeed, placed anywhere between the Y piece and the patient). Such alternative placements still avoid the negative effects of the ventilator circuit.

In a second experiment, the arrangements of FIGS. 15A and 15B were used with a single commercially available ventilator (the T-Bird ventilator) together with three different commercially available nebulizers. The nebulizer actuation was examined in the "continuous" mode. The humidity feature for these ventilators was examined by performing the test both when the feature is active and when it is off. An expiratory line filter was also used (not shown). Table 2 summarizes the data (as a percentage of nebulizer charge). Clearly, the Portex nebulizer performed poorly under these conditions. The Aerotech and Aerogen nebulizers appeared to be relatively insensitive when delivering the aerosol (either gentamicin or vacomycin) to the humidity feature, although there is some benefit to having the humidity feature turned off and not active. Interestingly, the inhaled mass is similar for both antibiotics.

EXAMPLE 7

FIG. 16 shows one embodiment of a bench model which can be used with either a nebulizer (shown as a box attached at the Y piece of FIG. 16A) or an aerosol catheter (the arrow in FIG. 16B indicates the catheter can be positioned in the ET tube). FIG. 16 shows a ventilator circuit comprising i) an inspiratory line and an expiratory line coming from a ventilator (not shown) converging at a junction (typically a "T" or "Y" junction). The endotracheal tube (or tracheostomy tube), instead of being in the patient, is attached to 100 ml tube, which models the proximal airways (trachea and mainstem bronchi); the 100 ml tube is attached to the inhaled mass filter. In other words (describing the arrangement moving in the direction of the patient), the Y piece is connected to the ET tube, which is connected to the 100 ml tube, which is attached to the inhaled mass filter (the filter measures aerosol that will pass out of the proximal airways and enter the distal lung).

In a first experiment, the bench model of FIG. 16B was tested with an aerosol catheter (the Trudell catheter, Trudell Medical International); a standard Y-piece was used (without any nebulizer). Radiolabeled albuterol aerosol was generated and introduced via the catheter into the ET tube. The inhaled mass was measured in two parts: the proximal ariways (100 ml tube) and distal airways (filter distal to the 100 ml tube). The Mass Median Aerodynamic Diameter (MMAD) was measured in aerosol delivered to distal airways using a cascade impactor. The test was performed with two different ventilators with the humidity feature active and off. Administration of the aerosol was continuous (not breath actuated). The results are shown in Table 3. The data reveal that administration of aerosol in this manner is relatively insensitive to humidity. Interestingly, the majority of drug is deposited in the 100 ml tube (modeling the proximal airlways) with smaller amounts in the filter (distal lung). These data suggest that the ET tube and trachea will be major sites of deposition when the delivery end of the catheter is within the ET tube. The results suggest delivery to the distal airways is comparable to that achieved with the nebulizer.

In a second experiment, a Trudell catheter was used to administer aerosol into the ET tube in a breath actuated mode using the bench model of FIG. 16B (again no nebulizer was used) and a single ventilator. Inhaled mass was measured using only the filter (a second filter in the expiratory line was also used). Both albuterol and gentamicin were tested. The results are shown in Table 4 and reveal that the Trudell catheter behaves in a manner that is largely independent of the conditions set by the ventilator (e.g. humidity). Breath actuation clearly increased the inhaled mass and the narrow range of deposition shows that this mode of administration provides good control over the dose.

Attempts to administer vancomycin in the same manner as gentamicin encountered difficulties; vancomycin can cause blockages of the catheter when operated in the breath actuated or pulsed mode. On the other hand, vancomycin aerosols have been successfully created in the continuous mode of operation using existing formulations.

EXAMPLE 8

Figure 17A:
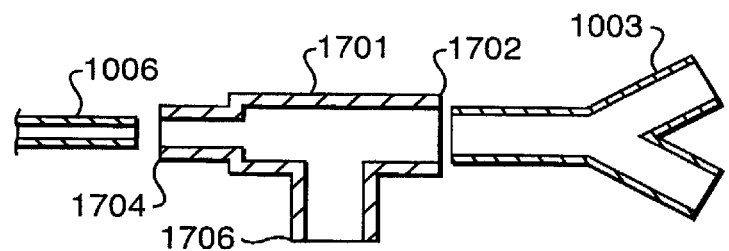
FIG. 17A shows a one piece adapter configured on a first end for attachment to a Y-piece, configured on a second end for attachment to an endotracheal tube (or tracheostomy tube), and configured on a third end (or "stem") for attachment to a nebulizer.

FIG. 17 shows various embodiments of a device for attaching a nebulizer to a ventilator circuit. The device can be generally characterized as a single piece of tubing or conduit, said device comprising two or three open ends (optionally, said ends have different inner diameters) and permitting fluidic communication between the elements attached to said ends. FIG. 17A shows a one piece adapter (1701) configured on a first end (1702) for attachment to a Y-piece (1703), configured on a second end (1704) for attachment to an endotracheal tube (1705) (or tracheostomy tube), and configured on a third end (or "stem") (1706) for attachment to a nebulizer (not shown). It is not intended that the present invention be limited to the particular attachment means. In one embodiment, attachment is achieved using tubing of different diameters. For example, FIG. 17A shows the tubing of the endotracheal tube (1705) has a smaller diameter than the second end (1704) of the adapter (1701) so that it can slide in and engage the adapter (1701). Alternatively, the adapter end could have a smaller diameter and could slide inside the ET tube. While not limited to precise dimensions, in one embodiment, the outer diameter of the endotracheal tube (1705) is approximately 15 mm and the inner dimension of the second end (1704) of the adapter (1701) is approximately 15 mm to create a tight male/female friction fit. Again, while not limited to precise dimensions, in one embodiment, the outer diameter of the Y-piece stem is 22 mm and the inner diameter of the first end (1702) of the adapter (1701) is 22 mm. Alternatively, the attachments can be snap fit or screw fit (e.g. one or more ends of the adapter are threaded).

Figure 17B:
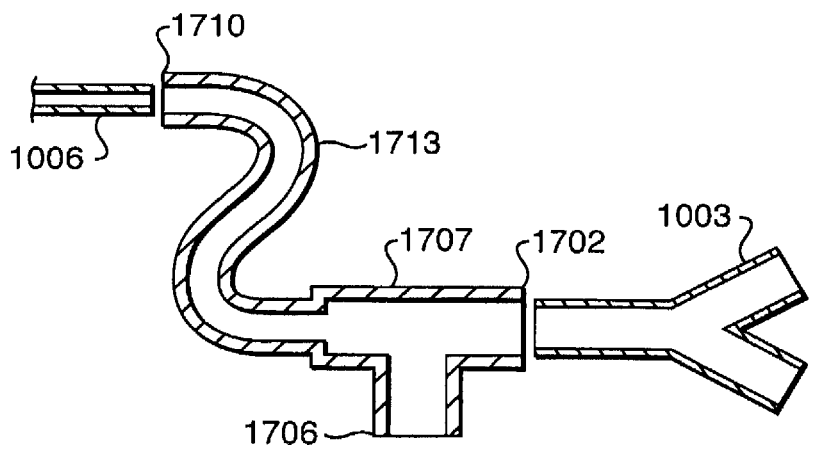
FIG. 17B shows a one piece adapter configured on a first end for attachment to a Y-piece, configured on a second end for attachment to an endotracheal tube (or tracheostomy tube), and configured on a third end (or "stem") for attachment to a nebulizer, wherein said second end comprises a flexible section.

FIG. 17B shows a one piece adapter (1707) configured on a first end (1708) for attachment to a Y-piece (1709), configured on a second end (1710) for attachment to an endotracheal tube (or tracheostomy tube) (1711), and configured on a third end (1712) (or "stem") for attachment to a nebulizer (not shown), wherein said second end (1710) comprises a flexible section (1713). It is not intended that the present invention be limited to the particular attachment means. In one embodiment, attachment is achieved using tubing of different diameters. For example, FIG. 17B shows the tubing of the endotracheal tube (1711) has a smaller diameter than the second end (1710) of the adapter (1707) so that it can slide in and engage the adapter (1707) in a male/female friction fit. Alternatively, the adapter end diameter could be smaller and could slide inside the ET tube. Alternatively, the attachments can be snap fit or screw fit (e.g. one or more ends of the adapter are threaded).

Figure 17C:
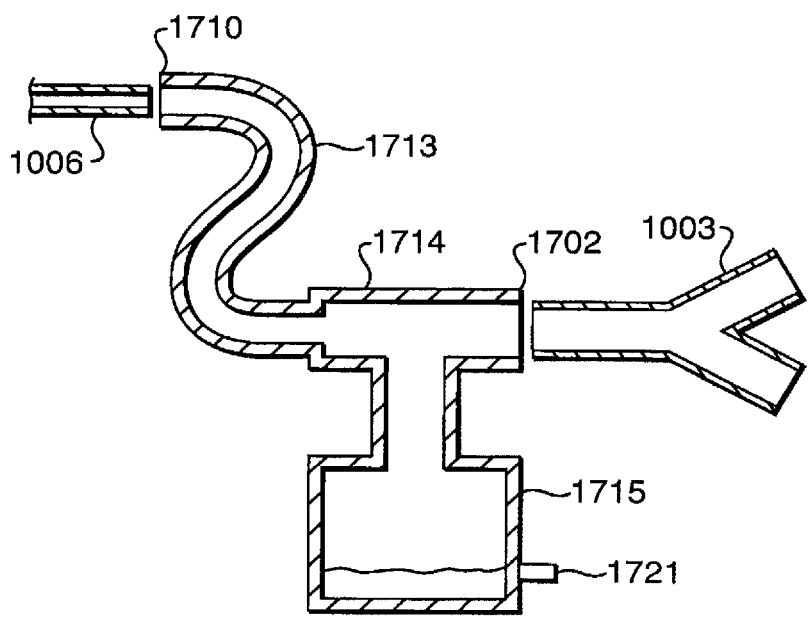
FIG. 17C shows a one piece adapter with an integral nebulizer, said adapter configured on a first end for attachment to a Y-piece, and configured on a second end for attachment to an endotracheal tube (or tracheostomy tube), wherein said second end comprises a flexible section.

FIG. 17C shows a one piece adapter (1714) with an integral nebulizer (1715), said adapter (1714) configured on a first end (1716) for attachment to a Y-piece (1717), and configured on a second end (1718) for attachment to an endotracheal tube (or tracheostomy tube) (1719), wherein said second end (1718) comprises a flexible section (1720). It is not intended that the present invention be limited to the particular attachment means. In one embodiment, attachment is achieved using tubing of different diameters. For example, FIG. 17C shows the tubing of the endotracheal tube (1711) has a smaller diameter than the second end (1710) of the adapter (1707) so that it can slide in and engage the adapter (1707) in a male/female friction fit. Alternatively, the adapter end diameter could be smaller such that it could slide inside the ET tube. Alternatively, the attachments can be snap fit or screw fit (e.g. one or more ends of the adapter are threaded).

The adapter (1714) shown in FIG. 17C could be molded as a single unit (the nebulizer as an integral part). Alternatively, the adapter (1714) could be molded as two (or more) parts (e.g. the nebulizer is molded separately and thereafter attached). The nebulizer could be drug loaded or empty. The nebulizer can have one or more ports (1721) for application of gas or liquid.

TABLE 1

DISTAL 'Y' CONFIGURATION SUMMARY OF AEROSOL DELIVERY (albuterol)

| VENT (nebulization mode) | HUMIDITY | Inhaled Mass | Expiratory | Neb Residual | RECOVERY |
|---|---|---|---|---|---|
| | | (as a % Neb Charge) | | | |
| T-BIRD | OFF | 12.4 | 41.1 | 36.4 | 89.9 |
| (continuous) | | 11.6 | 40.0 | 37.2 | 88.8 |
| | ON | 8.9 | 34.9 | 36.4 | 80.2 |
| | | 9.2 | 36.5 | 33.5 | 79.2 |
| DRAGER | OFF | 12.6 | 43.7 | 34.5 | 90.8 |
| (continuous) | | 12.6 | 42.5 | 35.6 | 90.7 |
| | ON | 8.7 | 40.0 | 34.6 | 83.3 |
| | | 8.1 | 34.9 | 39.9 | 82.9 |
| DRAGER | OFF | 13.5 | 23.9 | 52.2 | 89.6 |
| (breath | | 10.8 | 18.3 | 61.0 | 90.1 |
| actuated) | ON | 10.2 | 19.6 | 52.4 | 82.2 |
| | | 9.9 | 19.1 | 51.1 | 80.1 |
| MEAN ± SE | | 10.7 ± 0.5 | 32.9 ± 2.8 | 42.1 ± 2.7 | 85.6 ± 1.4 |

TABLE 2

ANTIBIOTICS SUMMARY (NEBULIZER AT DISTAL "Y" POSITION)

| VENTILATOR | NEBULIZER | HUMIDITY (n) | ANTIBIOTICS | % of INHALED MASS | % of EXPIRATORY FILT. | MMAD |
|---|---|---|---|---|---|---|
| T-BIRD | AEROTECH | OFF (1) | GENTAMICIN | 9.5 | 24.6 | 0.9 |
| | | ON (1) | | 6.2 | 23.7 | 1.3 |
| | | OFF (1) | VANCOMYCIN | 8.3 | 24.2 | 1.7 |
| | | ON (1) | | 6.1 | 25.2 | 1.1 |
| | AEROGEN | OFF (1) | GENTAMICIN | 13 | 18.9 | 1.1 |
| | | ON (1) | | 9 | 22.3 | 1.2 |
| | | OFF (1) | VANCOMYCIN | 10 | 16.3 | 2 |
| | | ON (1) | | 11.2 | 18.2 | 2 |
| | PORTEX | ON (1) | GENTAMICIN | 3.1 | 11.8 | 0.9 |
| | | ON (1) | VANCOMYCIN | 2.1 | 7.9 | 1.1 |

TABLE 3

| | | | Inhaled Mass | | | |
|---|---|---|---|---|---|---|
| Ventilator | Humidity | n | Distal airways | Proximal airways | % Recovered | MMAD |
| T-Bird | off | 12 | 7.4 ± 0.5 | 68.0 ± 3.0 | 98.0 ± 1.2 | 1.12 ± 0.2 |
| T-Bird | on | 12 | 8.0 ± 0.5 | 68.7 ± 3.8 | 92.0 ± 2.9 | 1.72 ± 0.2 |
| Drager | off | 3 | 7.3 ± 1.1 | 70.0 ± 9.4 | 93.0 ± 3.5 | 1.23 ± 0.1 |
| Drager | on | 3 | 7.8 ± 1.7 | 68.0 ± 8.3 | 90.0 ± 3.5 | 1.30 ± 0.2 |

All values MEAN ± SEM

TABLE 4

Endo Tracheal Catheter Nebulization System (ETCNS-breath actuated)

| VENT | CONDITION (n) | DRUG | Inhaled Mass % Nebulizer | Expiratory Charge | Residual % | TOTAL % Recovered |
|---|---|---|---|---|---|---|
| T-BIRD | DRY (4) | ALBUTEROL | 23.1 | 6.9 | 0.8 | 30.8 |
| | | | 23.7 | 6.0 | 2.4 | 32.1 |
| | | | 24.3 | 5.5 | 2.3 | 32.1 |
| | | | 24.6 | 3.9 | 2.7 | 31.2 |
| | MEAN ± SE | | 23.9 ± 0.3 | 5.6 ± 0.6 | 2.0 ± 0.4 | 31.6 ± 0.3 |
| | HUMID(3) | ALBUTEROL | 21 | 1.5 | 2.9 | 25.4 |
| | | | 24.3 | 1.7 | 2.3 | 28.3 |
| | | | 26 | 1.4 | 1.1 | 28.5 |
| | MEAN ± SE | | 23.8 ± 1.5 | 1.5 ± 0.09 | 2.1 ± 0.5 | 27.4 ± 1.0 |
| | DRY (1) | GENTAMICIN | 25.9 | 6.3 | 0.2 | 32.4 |
| | HUMID(1) | | 19.1 | 3.6 | 3.6 | 26.3 |
| | HUMID(1) | | 22.5 | 2.9 | 1.8 | 27.2 |

The invention claimed is:

1. A device comprising: a) a T-piece connected to b) an aerosol generator configured for breath actuation, said aerosol generator comprising i) a reservoir comprising fluid, said fluid comprising an antibiotic, ii) a vibrational element, and iii) a dome-shaped aperture plate with tapered holes, wherein said T-piece is attached to a junction of a ventilation circuit, wherein said junction comprises a Y-piece comprising a first end attached to an inspiratory line of said ventilator circuit, a second end attached to an expiratory line of said ventilator circuit, and a stem attached to an endotracheal tube, wherein said T-piece is attached to said stem.

2. The device of claim 1, wherein said antibiotic comprises amikacin.

3. A method of attaching and activating an aerosol generator, comprising:
   A) providing a) a ventilation circuit comprising a Y-piece, wherein said Y-piece comprises a first end attached to an inspiratory line of said ventilator circuit, a second end attached to an expiratory line of said ventilator circuit, and a stem attached to an endotracheal tube, said endotracheal tube connected to a patient, and b) a device comprising a T-piece connected to an aerosol generator, said aerosol generator comprising i) a reservoir comprising fluid, said fluid comprising antibiotic, ii) a vibrational element, and iii) a dome-shaped aperture plate with tapered holes;
   B) attaching said T-piece to the stem of said Y-piece, thereby attaching said aerosol generator to said ventilation circuit; and
   C) activating said aerosol generator under conditions of breath actuation wherein the plate vibrates, causing fluid in said reservoir to be drawn through the tapered holes and into said Y-piece, creating an aerosol with a defined range of droplet sizes.

4. The method of claim 3, wherein said antibiotic comprises amikacin.

5. The method of claim 3, wherein said activating of step c) is done after the patient has been connected to the ventilation circuit for greater than three days without testing the patient for bacterial infection.

6. The method of claim 3, wherein said activating of step c) is done after the patient has been connected to the ventilation circuit for greater than five days without testing the patient for bacterial infection.

7. The method of claim 3, wherein said activating of step c) is done after the patient has been connected to the ventilation circuit for greater than seven days without testing the patient for bacterial infection.

8. The method of claim 3, wherein said patient, prior to step c), was given antibiotic systemically.

9. A method of attaching and activating an aerosol generator, comprising:
   A) providing a) a ventilation circuit comprising a Y-piece, wherein said Y-piece comprises a first end attached to an inspiratory line of said ventilator circuit, a second end attached to an expiratory line of said ventilator circuit, and a stem attached to an endotracheal tube, said endotracheal tube connected to a patient, and b) a device comprising a T-piece connected to an aerosol generator, said aerosol generator comprising a reservoir comprising fluid, said fluid comprising antibiotic;
   B) attaching said T-piece to the stem of said Y-piece, thereby attaching said aerosol generator to said ventilation circuit; and
   C) activating said aerosol generator under conditions of breath actuation, causing aerosolized antibiotic to be drawn into said Y-piece and said patient during inspiration by said patient such that a more reproducible dose is delivered as compared to the dose delivered using the arrangement where the aerosol generator is in the inspiratory line.

10. The method of claim 9, wherein said activating of step c) is done after the patient has been connected to the ventilation circuit for greater than three days without testing the patient for bacterial infection.

11. The method of claim 9, wherein said activating of step c) is done after the patient has been connected to the ventilation circuit for greater than five days without testing the patient for bacterial infection.

12. The method of claim 9, wherein said activating of step c) is done after the patient has been connected to the ventilation circuit for greater than seven days without testing the patient for bacterial infection.

13. The method of claim 9, wherein said patient is an intubated patient exhibiting one or more symptoms of microbial infection and after step C), one or more symptoms are reduced.

14. The method of claim 9, wherein said patient, prior to step c), was given antibiotic systemically.

* * * * *